(12) United States Patent
Li et al.

(10) Patent No.: US 11,512,326 B2
(45) Date of Patent: Nov. 29, 2022

(54) SMALL ANGIOTENSIN PEPTIDE EXPRESSION SYSTEM IN MAMMALIAN CELLS

(75) Inventors: Qiuhong Li, Gainesville, FL (US); William W. Hauswirth, Gainesville, FL (US); Alfred S. Lewin, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 13/321,104

(22) PCT Filed: May 26, 2010

(86) PCT No.: PCT/US2010/036153
§ 371 (c)(1),
(2), (4) Date: Mar. 5, 2012

(87) PCT Pub. No.: WO2010/138555
PCT Pub. Date: Dec. 2, 2010

(65) Prior Publication Data
US 2012/0157513 A1    Jun. 21, 2012

Related U.S. Application Data

(60) Provisional application No. 61/181,036, filed on May 26, 2009.

(51) Int. Cl.
| | |
|---|---|
| C12N 15/86 | (2006.01) |
| A61K 48/00 | (2006.01) |
| C12P 21/02 | (2006.01) |
| C07K 7/14 | (2006.01) |
| A61K 38/00 | (2006.01) |

(52) U.S. Cl.
CPC ............... *C12N 15/86* (2013.01); *C07K 7/14* (2013.01); *C12P 21/02* (2013.01); *A61K 38/00* (2013.01); *A61K 48/00* (2013.01); *C07K 2319/00* (2013.01); *C07K 2319/31* (2013.01); *C07K 2319/50* (2013.01); *C07K 2319/60* (2013.01); *C12N 2750/14143* (2013.01)

(58) Field of Classification Search
CPC ........... C07K 7/14; C12N 15/86; C12N 2750/14143; C12P 21/02; A61K 38/00; A61K 48/00
See application file for complete search history.

(56) References Cited

U.S. PATENT DOCUMENTS

| | | | |
|---|---|---|---|
| 5,643,758 A * | 7/1997 | Guan et al. | 435/69.7 |
| 6,451,594 B1 | 9/2002 | Chien et al. | |
| 7,071,172 B2 | 7/2006 | McCown et al. | |
| 7,306,944 B2 | 12/2007 | Choi et al. | |
| 8,962,567 B2 | 2/2015 | Choi et al. | |
| 11,053,291 B2 | 7/2021 | Ildefonso et al. | |
| 2003/0045498 A1 | 3/2003 | Kovesdi et al. | |
| 2003/0171267 A1 * | 9/2003 | Rosen | A61K 9/0019 |
| | | | 435/69.7 |
| 2003/0236396 A1 | 12/2003 | Fasel et al. | |
| 2004/0063635 A1 * | 4/2004 | Yu et al. | 514/12 |
| 2005/0142130 A1 * | 6/2005 | Roks et al. | 424/94.64 |
| 2007/0031410 A1 | 2/2007 | Harton et al. | |
| 2009/0148894 A1 * | 6/2009 | Broedel | C12N 15/67 |
| | | | 435/69.1 |
| 2009/0239259 A1 | 9/2009 | Hsieh | |
| 2010/0029012 A1 | 2/2010 | Kern et al. | |
| 2010/0120665 A1 | 5/2010 | Kaleko et al. | |
| 2010/0209447 A1 | 8/2010 | Kumar-Singh et al. | |
| 2013/0310443 A1 | 11/2013 | Srivastava et al. | |
| 2016/0376325 A1 | 12/2016 | McFadden et al. | |
| 2017/0088593 A1 | 3/2017 | Ildefonso et al. | |
| 2021/0300978 A1 | 9/2021 | Ildefonso et al. | |

FOREIGN PATENT DOCUMENTS

| | | | | |
|---|---|---|---|---|
| EP | 399 666 A1 | 4/1990 | | |
| EP | 413 622 A1 | 2/1991 | | |
| WO | WO 93/15199 A1 | 8/1993 | | |
| WO | WO 93/15200 A1 | 8/1993 | | |
| WO | WO 02/26780 A2 | 4/2002 | | |
| WO | WO-03078648 A2 * | 9/2003 | ............ | C07K 14/47 |
| WO | WO-2007014162 * | 2/2007 | ............ | C07K 16/00 |
| WO | 2008/000445 | 1/2008 | | |
| WO | WO 2008/057434 A2 | 5/2008 | | |
| WO | WO 2010/138555 A2 | 12/2010 | | |

(Continued)

OTHER PUBLICATIONS

Chan et al. (Mol Ther, 11 (1): 120-31, 2005).*
Multhoff (Methods 43 (2007) 229-237). (Year: 2007).*
Foti (Thesis, 1-180, 2008) (Year: 2008).*
International Search Report, PCT/US2010/036153, dated Mar. 23, 2011.
International Preliminary Report on Patentability for International Application No. PCT/US2010/036153 dated Dec. 8, 2011.
International Search Report and Written Opinion for International Application No. PCT/US2015/016638 dated May 18, 2015.
International Preliminary Report on Patentability for International Application No. PCT/US2015/016638 dated Sep. 1, 2016.

(Continued)

*Primary Examiner* — Anoop K Singh
*Assistant Examiner* — Magdalene K Sgagias
(74) *Attorney, Agent, or Firm* — Wolf, Greenfield & Sacks, P.C.

(57) ABSTRACT

The present invention is directed to a delivery vector for transferring a small peptide coding sequence to a cell for expression of the small peptide coding sequence within the cell. The delivery vector comprises a secretory signal sequence; a sequence encoding a carrier protein operatively associated with the secretory signal sequence; a sequence encoding a cleavage site operatively associated with the sequence encoding a carrier protein; and a sequence encoding a small peptide operatively associated with the sequence encoding a cleavage site.

11 Claims, 12 Drawing Sheets

Specification includes a Sequence Listing.

(56) References Cited

FOREIGN PATENT DOCUMENTS

| WO | WO 2013/012806 A2 | 1/2013 |
|---|---|---|
| WO | WO 2013/067036 A1 | 5/2013 |
| WO | WO 2013/090318 A1 | 6/2013 |
| WO | WO 2014/005219 A1 | 1/2014 |
| WO | WO 2014/076702 A1 | 5/2014 |

OTHER PUBLICATIONS

Extended European Search Report for Application No. EP 15752059.4 dated Jul. 7, 2017.

International Search Report for International Application No. PCT/US2015/020001 dated Jun. 24, 2015.

International Preliminary Report on Patentability for International Application No. PCT/US2015/020001 dated Sep. 22, 2016.

Supplementary European Search Report for European Application No. EP 15761543.6 dated Jul. 28, 2017.

Abed et al., Discovery of direct inhibitors of Keap1-Nrf2 protein-protein interaction as potential therapeutic and preventive agents. Acta Pharm Sin B. Jul. 2015;5(4):285-99. doi: 10.1016/j.apsb.2015.05.008. Epub Jul. 2, 2015. Review.

Alhakamy et al., Noncovalently associated cell-penetrating peptides for gene delivery applications. Ther Deliv. Jun. 2013;4(6):741-57. doi: 10.4155/tde.13.44. Review.

Chumanov et al., Expression, purification, and refolding of active Nrf2 transcription factor fused to protein transduction TAT tag. Protein Expr Purif. Dec. 2010;74(2):280-8. doi: 10.1016/j.pep.2010.06.017. Epub Jul. 1, 2010.

Daya et al., Gene therapy using adeno-associated virus vectors. Clin Microbiol Rev. Oct. 2008;21(4):583-93. doi: 10.1128/CMR.00008-08.

Déglon et al., Self-inactivating lentiviral vectors with enhanced transgene expression as potential gene transfer system in Parkinson's disease. Hum Gene Ther. Jan. 1, 2000; 11(1): 179-90.

Foti et al., Delivering multiple gene products in the brain from a single adeno-associated virus vector. Gene Ther. Nov. 2009;16(11):1314-9. doi: 10.1038/gt.2009.106. Epub Sep. 3, 2009.

Handa et al., How does the macula protect itself from oxidative stress? Mol Aspects Med. Aug. 2012;33(4):418-35. doi: 10.1016/j.mam.2012.03.006. Epub Apr. 5, 2012. Author manuscript.

Ildefonso et al., Targeting the Nrf2 Signaling Pathway in the Retina With a Gene-Delivered Secretable and Cell-Penetrating Peptide. Invest Ophthalmol Vis Sci. Feb. 2016;57(2):372-86. doi:10.1167/iovs.15-17703.

Jacobson et al., Safety of recombinant adeno-associated virus type 2-RPE65 vector delivered by ocular subretinal injection. Mol Ther. Jun. 2006;13(6):1074-84. Epub Apr. 27, 2006.

Johnston et al., A poxvirus-encoded pyrin domain protein interacts with ASC-1 to inhibit host inflammatory and apoptotic responses to infection. Immunity. Dec. 2005;23(6):587-98. Erratum in: Immunity. Oct. 2006;25(4):687. Ricuttio, Dan [corrected to Ricciuto, Dan].

Kanninen et al., Intrahippocampal injection of a lentiviral vector expressing Nrf2 improves spatial learning in a mouse model of Alzheimer's disease. Proc Natl Acad Sci U S A. Sep. 22, 2009;106(38):16505-10. doi: 10.1073/pnas.0908397106. Epub Sep. 10, 2009.

Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.

Koren et al., Cell-penetrating peptides: breaking through to the other side. Trends Mol Med. Jul. 2012;18(7):385-93. doi: 10.1016/j.molmed.2012.04.012. Epub Jun. 7, 2012.

Le et al., Pyrin- and CARD-only Proteins as Regulators of NLR Functions. Front Immunol. Sep. 17, 2013;4:275. doi: 10.3389/fimmu.2013.00275.

Lee et al., NF-E2-related factor-2 mediates neuroprotection against mitochondrial complex I inhibitors and increased concentrations of intracellular calcium in primary cortical neurons. J Biol Chem. Sep. 2, 20036;278(39):37948-56. Epub Jul. 3, 2003.

Liu et al., The immunoregulatory properties of oncolytic myxoma virus and their implications in therapeutics. Microbes Infect. Dec. 2010;12(14-15):1144-52. doi: 10.1016/j.micinf.2010.08.012. Epub Sep. 9, 2010. Author manuscript.

Lucas et al., Secreted immunomodulatory viral proteins as novel biotherapeutics. J Immunol. Oct. 15, 2004;173(8):4765-74.

Rahman et al., Co-regulation of NF-kappaB and inflammasome-mediated inflammatory responses by myxoma virus pyrin domain-containing protein M013. PLoS Pathog. Oct. 2009;5(10):e1000635. doi: 10.1371/journal.ppat.1000635. Epub Oct. 23, 2009.

Rahman et al., Myxoma virus lacking the pyrin-like protein M013 is sensed in human myeloid cells by both NLRP3 and multiple Toll-like receptors, which independently activate the inflammasome and NF-κB innate response pathways. J Virol. Dec. 2011;85(23):12505-17. doi: 10.1128/JVI.00410-11. Epub Sep. 28, 2011.

Rahman et al., Myxoma virus protein M029 is a dual function immunomodulator that inhibits PKR and also conscripts RHA/DHX9 to promote expanded host tropism and viral replication. PLoS Pathog. 2013;9(7):e1003465. doi: 10.1371/journal.ppat.1003465. Epub Jul. 4, 2013.

Smith et al., Vaccinia virus immune evasion: mechanisms, virulence and immunogenicity. J Gen Virol. Nov. 2013;94(Pt 11):2367-92. doi: 10.1099/vir.0.055921-0. Epub Sep. 2, 2013.

Steel et al., Anti-inflammatory Effect of a Cell-Penetrating Peptide Targeting the Nrf2/Keap1 Interaction. ACS Med Chem Lett. May 10, 2012;3(5):407-410. Epub Mar. 12, 2012.

Stöckli et al., Molecular cloning, expression and regional distribution of rat ciliary neurotrophic factor. Nature. Dec. 21-28, 1989;342(6252):920-3.

Taxman et al., Inflammasome inhibition as a pathogenic stealth mechanism. Cell Host Microbe. Jul. 22, 2010;8(1):7-11. doi: 10.1016/j.chom.2010.06.005.

Waehler et al., Engineering targeted viral vectors for gene therapy. Nat Rev Genet. Aug. 2007;8(8):573-87. Epub Jul. 3, 2007.

Zhao et al., A novel strategy to activate cytoprotective genes in the injured brain. Biochem Biophys Res Commun. Apr. 15, 2011;407(3):501-6. doi: 10.1016/j.bbrc.2011.03.046. Epub Mar. 22, 2011.

Giove et al., Transduction of the inner mouse retina using AAVrh8 and AAVrh10 via intravitreal injection. Exp Eye Res. Nov. 2010;91(5):652-9. doi: 10.1016/j.exer.2010.08.011. Epub Aug. 17, 2010. Author manuscript.

Naso et al., Adeno-Associated Virus (AAV) as a Vector for Gene Therapy. BioDrugs. Aug. 2017;31(4):317-334. doi: 10.1007/s40259-017-0234-5.

Pang et al., Comparative analysis of in vivo and in vitro AAV vector transduction in the neonatal mouse retina: effects of serotype and site of administration. Vision Res. Feb. 2008;48(3):377-85. Epub Oct. 22, 2007.

U.S. Appl. No. 17/353,120, filed Jun. 8, 2021, Ildefonso et al.

[No Author Listed], Swiss-Protein Accession No. P26992 (Signal Peptide Database). 2008; 4 pages.

Chen et al., Distribution, markers, and functions of retinal microglia. Ocul Immunol Inflamm. Mar. 2002;10(1):27-39. doi: 10.1076/ocii.10.1.27.10328.

Negro et al., Cloning and expression of human ciliary neurotrophic factor. Eur J Biochem. Oct. 1, 1991;201(1):289-94. doi: 10.1111/j.1432-1033.1991.tb16286.x.

Petrs-Silva et al., High-efficiency transduction of the mouse retina by tyrosine-mutant AAV serotype vectors. Mol Ther. Mar. 2009;17(3):463-71. doi: 10.1038/mt.2008.269. Epub Dec. 16, 2008.

Petrs-Silva et al., Novel properties of tyrosine-mutant AAV2 vectors in the mouse retina. Mol Ther. Feb. 2011;19(2):293-301. doi: 10.1038/mt.2010.234. Epub Nov. 2, 2010.

Solinis et al., Treatment of ocular disorders by gene therapy. Eur J Pharm Biopharm. Sep. 2015;95(Pt B):331-42. doi: 10.1016/j.ejpb.2014.12.022. Epub Dec. 20, 2014.

Zhao et al., Age-related retinopathy in NRF2-deficient mice. PLoS One. Apr. 29, 2011;6(4):e19456. doi: 10.1371/journal.pone.0019456.

(56) References Cited

OTHER PUBLICATIONS

Flotte et al., Preclinical characterization of a recombinant adeno-associated virus type 1-pseudotyped vector demonstrates dose-dependent injection site inflammation and dissemination of vector genomes to distant sites. Hum Gene Ther. Mar. 2007;18(3):245-56. doi: 10.1089/hum.2006.113.

Jones et al., Cell entry of cell penetrating peptides: tales of tails wagging dogs. J Control Release. Jul. 20, 2012;161(2):582-91. doi: 10.1016/j.jconrel.2012.04.003. Epub Apr. 10, 2012.

Koerber et al., Molecular evolution of adeno-associated virus for enhanced glial gene delivery. Mol Ther. Dec. 2009;17(12):2088-95. doi: 10.1038/mt.2009.184. Epub Aug. 11, 2009.

Lindqvist et al., Retinal glial (Müller) cells: sensing and responding to tissue stretch. Invest Ophthalmol Vis Sci. Mar. 2010;51(3):1683-90. doi: 10.1167/iovs.09-4159. Epub Nov. 5, 2009.

Sakamoto et al., Inhibition of experimental proliferative vitreoretinopathy by retroviral vector-mediated transfer of suicide gene. Can proliferative vitreoretinopathy be a target of gene therapy? Ophthalmology. Oct. 1995;102(10):1417-24. doi: 10.1016/s0161-6420(95)30850-0.

Tréhin et al. Chances and pitfalls of cell penetrating peptides for cellular drug delivery. Eur J Pharm Biopharm. Sep. 2004;58(2):209-23. doi: 10.1016/j.ejpb.2004.02.018.

\* cited by examiner

SMALL ANGIOTENSIN PEPTIDE EXPRESSION SYSTEM IN MAMMALIAN CELLS

CROSS-REFERENCE TO RELATED APPLICATIONS

This application is related to U.S. Provisional Application No. 61/181,036 filed May 26, 2009 to which priority is claimed under 35 USC 119.

GOVERNMENT SUPPORT

This work was supported by NIH grant R01-EY11123. The government has certain rights in this invention.

FIELD OF THE INVENTION

The present invention relates to methods for providing a continuous supply of small bioactive peptides through gene delivery.

BACKGROUND

Bioactive small peptides, either occurring naturally or produced synthetically, have gained increasing interest as research tools and as pharmacological drugs in recent years. In particular, these bioactive small peptides may play key roles in various physiological, as well as pathological processes, and thus are promising targets for therapeutic interventions for many pathological conditions. Further, bioactive small peptides have gained use as agonists and/or antagonists of various biological processes with enhanced target affinity and specificity compared to conventional agents. For example, numerous small peptides have been developed that target pathological processes, such as cancer, tumor-specific angiogenesis, and pathogenic apoptosis in neurodegenerative disorders. Despite these advances, the use of small peptides as mainstream drug candidates has been hampered by their low bioavailability (due primarily to small peptides' poor permeability across the cell membrane); short half-life in cells (due primarily to the small peptides' susceptibility to cellular proteases for degradation); and immune responses triggered by repeated administration (due to the nature of the small peptide).

One strategy that has been developed to overcome these problems of exogenous administration of small peptides is to produce the small peptide intracellularly by using high-expression vectors to generate sufficient levels of the therapeutic small peptides in the cell/tissue of interest. However, expressing small peptides in mammalian cells has been challenging due to some of the same reasons that have hampered the use of small peptides as mainstream drug candidates. In spite of these problems, many researchers have employed different expression systems to express the small peptide as part of a fusion peptide with scaffold proteins or other reporter proteins, such as green fluorescent protein (GFP). This strategy may be useful for peptides that maintain their biological activity and function after fusion, but useless for many small peptides that are only active in their free peptide forms.

DETAILED DESCRIPTION OF THE INVENTIONS

Figure 1:
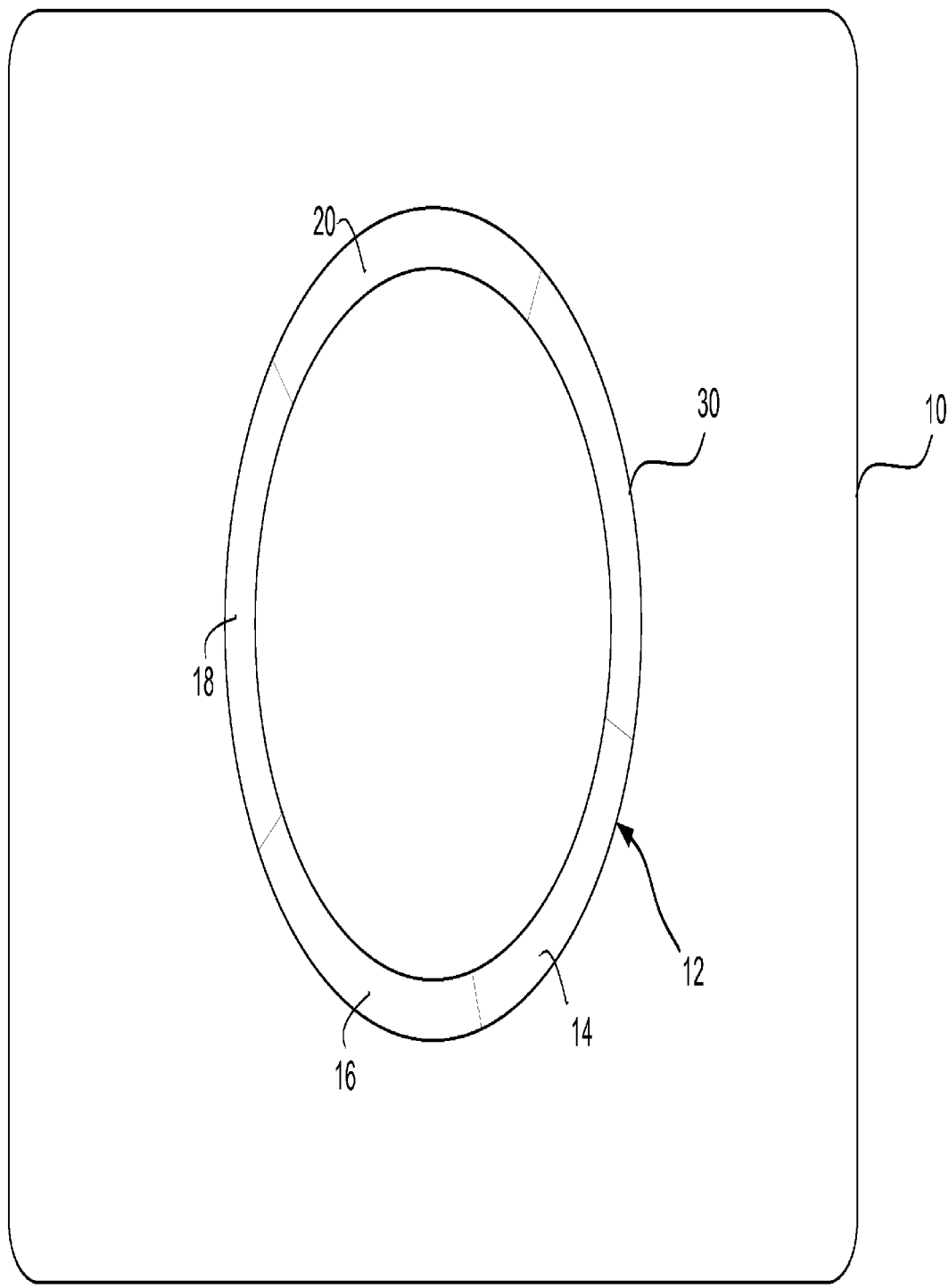
FIG. 1 depicts a delivery vector in accordance with an aspect of the present invention.

The present inventors have developed novel and nonobvious processes for producing bioactive small peptides of interest through delivery to target cells. Advantageously, aspects of the present invention allow the small peptide of interest to be expressed as the product of a large precursor protein, which is cleavable to release the small peptide to cells surrounding the area of transduction, or to release the small peptide to the systemic circulation or the lymph system.

In accordance with one aspect of the present invention, there is provided a delivery vector for transferring a small peptide coding sequence to a cell for expression of the small peptide coding sequence within the cell. The delivery vector comprises: (i) a secretory signal sequence; (ii) a sequence encoding a carrier protein operatively associated with the secretory signal sequence; (iii) a sequence encoding a cleavage site operatively associated with the sequence encoding a carrier protein; and (iv) a sequence encoding a small peptide operatively associated with the sequence encoding a cleavage site.

In accordance with another aspect of the present invention, the present invention provides for a pharmaceutical composition comprising the delivery vector as described herein in combination with a pharmaceutically acceptable carrier. Conventional procedures and ingredients for the selection and preparation of suitable pharmaceutical formulations are described, for example, in Remington's Pharmaceutical Sciences and in The United States Pharmacopeia: The National Formulary (USP 24 NF19) published in 1999.

In accordance with yet another aspect of the present invention, there is provided a method for producing a small peptide and secreting the small peptide from a target cell. The method comprises introducing a delivery vector into the target cell. The step of introducing results in the expression of a fusion polypeptide comprising the small peptide and secretion from the target cell to, for example, cells surrounding the area of transduction, or to deliver the small peptide extracellularly to circulation or lymph system. The delivery vector comprises (i) a secretory signal sequence; (ii) a sequence encoding a carrier protein operatively associated with the secretory signal sequence; (iii) a sequence encoding a cleavage site operatively associated with the sequence encoding a carrier protein; and (iv) a sequence encoding a small peptide operatively associated with the sequence encoding a cleavage site.

In accordance with still another aspect of the present invention, there is provided a method of producing a quantity of small peptides comprising administering a delivery vector as described herein into a cell resulting in the secretion of the small peptide.

Referring now to the drawings, there is illustrated a delivery vector 10 comprising an expression system 12 in accordance with the present invention. The expression system 12 comprises a promoter 14 and a coding sequence 16 for coding a fusion peptide comprising a small peptide, cleavable from the remainder of the fusion peptide.

The delivery vector 10 may be a viral or non-vector as is known in the art, including but not limited to, single-stranded and double-stranded nucleic acid vectors as well as DNA, RNA, and DNA/RNA chimeric vectors. Exemplary viral vectors include, but are not limited to, adenovirus, herpesvirus, lentivirus, parvovirus (e.g., AAV), baculovirus and Epstein Barr Virus vectors. Exemplary non-viral vectors include, but are not limited to, plasmid, phage, yeast artificial chromosomes (YACs), Bacterial Artificial Chromosomes (BACs), and naked DNA vectors (e.g., by liposomal delivery), or synthetic nucleotide vectors (e.g., vectors that are generated by PCR methods or oligonucleotide synthesis, as are known in the art). In one particular embodiment, the delivery vector 10 is an adeno-associated virus (AAV) vector, e.g., in the form of AAV viral particles. In another embodiment, the delivery vector 10 is a plasmid. Plasmids are "naked" DNA and do not encode genes necessary to encase the genetic material for transfer to a new host. The delivery vectors described herein may be used in both in vitro and in vivo studies. For example, in in vitro studies, the efficiency of the plasmid transfection can be monitored by GFP expression and the small peptide activity can be evaluated by a suitable biological assay.

Figure 2:
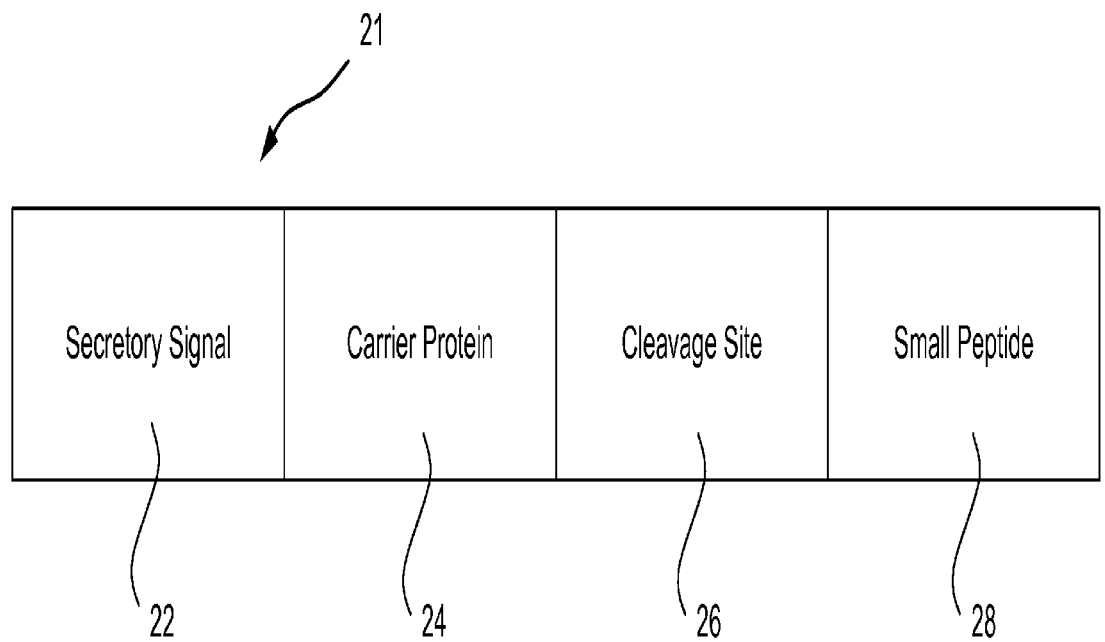
FIG. 2 depicts an expressed fusion polypeptide in accordance with an aspect of the present invention.

The expression system 12 comprises multiple sequences that when expressed may produce a fusion polypeptide as will be explained below. In one embodiment, as shown in FIG. 1, the expression system 12 comprises a secretory signal sequence 14 encoding for a secretory signal peptide; a sequence 16 encoding for a carrier protein operatively associated with the secretory signal sequence 14; a sequence 18 encoding for a protease cleavage site operatively associated with the sequence 16 encoding for a carrier protein; and a sequence 20 encoding for a small peptide operatively associated with the sequence 18 encoding for a protease cleavage site. As shown in FIG. 2, the resulting expressed fusion polypeptide 21 comprises (in a 5' to 3' direction) at least a secretory signal peptide 22, a carrier protein 24, a protease cleavage site 26, and a small peptide 28.

The secretory signal sequence 14 encoding for the secretory signal peptide 22 enables the expressed small peptide 28 of the fusion polypeptide 21 to be secreted extracellularly (or into the circulation if delivered systemically). By secreting the small peptide 28 extracellularly, the biological function of the small peptide 28 may be provided in the cells harboring the expression system 12, as well as to distant cells. In one embodiment, the secretory signal sequence 14 will be at the amino-terminus of the expression system 12 (e.g., the secretory signal sequence is 5' to the remaining portion of the expression system 12). Alternatively, in another embodiment, the secretory signal sequence 14 may be at the carboxy-terminus or embedded within the expression system 12 so long as the secretory signal sequence 14 is operatively associated with at least a portion of the expression system 12, and once expressed, directs secretion of the small peptide 28 from the target cell after cleavage of the small peptide 28 from the remainder of the expressed fusion polypeptide 21.

The secretory signal sequence 14 is operatively associated with another portion of the expression system 12 such that the expressed fusion polypeptide 21 is targeted to the secretory pathway of the cell into which the expression system 12 is delivered (the target cell). In addition, the secretory signal sequence 14 is operatively associated with another portion of the expression system 12 such that when expressed, the small peptide 28 is secreted from the cell at a higher level (e.g., a greater quantity) than in the absence of the secretory signal sequence 14. The degree, e.g., percentage, to which the secretory signal peptide 22 (encoded by the secretory signal sequence 14) directs the secretion of the remainder of the expressed fusion polypeptide 21 is not critical so long as the secretory signal peptide 22 provides a desired level of secretion and/or regulation of expression of the expressed fusion polypeptide 21. Examples of alternative secretory signal sequences are taught in U.S. Pat. Nos. 7,691,607 and 7,071,172.

The sequence 16 encoding for the carrier protein 24 may be for any suitable carrier protein known in the art. For example, the sequence 16 encoding for the carrier protein 24 may be a coding sequence for one or more of β-galactosidase, luciferase, chloramphenyl acetyltransferase, GUS (β-glucuronidase), and green flourescent protein (GFP) (from jelly fish). In other embodiments, the carrier is a relatively unreactive protein prevalent found in serum and/or tissues such as, but not limited to, albumin, alpha-1-antitrypsin, or proteoglycans. In one embodiment, the sequence 16 encoding for the carrier protein 24 is a sequence coding for GFP. The GFP can serve both as a spacer and reporter protein to monitor the expression level, cell/tissue and intracellular distribution of the expressed fusion polypeptide 21.

Generally, it is known that the smaller the peptide, the more difficult it is to express the small peptide in mammalian cells. There are believed to be at least two biological reasons for this phenomenon. First, the protein synthesis machinery of a cell, e.g., the ribosome complex, must bind any mRNA encoding the protein for translation. Generally, the smaller the peptide, the more difficult it will be to initiate translation, e.g., the more difficult it will be for the complex to bind to the mRNA. Second, mammalian cells have several surveillance mechanisms; one such surveillance mechanism is called nonsense-mediated decay. Nonsense-mediated decay recognizes short peptides being synthesized as aberrant or truncated protein products, and thus targets them for rapid degradation. For this reason, the in vivo production of small peptides has been problematic. One purpose of the sequence 16 encoding for the carrier protein 24 is to express a carrier protein portion that will add length to the fusion polypeptide chain. In this way, the expressed small peptide 28 will be part of the larger fusion polypeptide 21 until the small peptide 28 is cleaved and secreted from the cell.

To allow cleavage of the small peptide 28 from the remainder of the fusion polypeptide 21, the expression system 12 comprises the sequence 18 encoding for the protease cleavage site 26. The protease cleavage site 26 allows the small peptide 28 of the fusion polypeptide 21 to be cleaved precisely following expression and secretion as explained herein. In one embodiment, the sequence 18 encoding for the protease cleavage site 26 is a sequence encoding for a furin cleavage site. The furin cleavage site is based on the ubiquitous protease furin, which is present both in the Golgi network, as well as in the extracellular space of virtually all mammalian cell types. The present inventors have developed the novel, synthetic furin cleavage site after careful comparison of available natural protein substrates of furin protease, with enhanced affinity for furin cleavage.

Alternative cleavage sites/enzymes that may be used in accordance with the teachings herein include the following: (1). Proprotein/prohormone convertases—the other members of same family of furin. The conversion of inactive precursor proteins into bioactive neuropeptides and peptide hormones involves regulated secretory proteins of preprotein convertases. The proprotein convertases represent a family of nine proteinases, comprising seven basic amino acid-specific subtilisin-like serine proteinases related to yeast kexin, known as PC1/3, PC2, furin, PC4, PC5/6, PACE4 and PC7, and two other subtilases that cleave at non-basic residues, called SKI-1/S1P and NARC-1/PCSK9. While furin is ubiquitously expressed, others may have tissue specific distributions that may be used for targeting expression. (2). Thrombin and factor Xa: both commonly used to cleave fusion protein.

Alternative carrier proteins in addition to that discussed elsewhere herein include the following: (1). Heat-shock proteins-assisting the protein folding under stress conditions and (2). Secreted form of the receptor for Advanced Glycation End-product (AGE)-sRAGE. AGE is elevated under many pathological conditions including diabetes, oxidative stress, neurodegenerative diseases and aging. AGE exerts it deleterious effect via the receptor, RAGE, which leads to activation of many downstream signaling pathways. The soluble form of RAGE (sRAGE) may have beneficial effect by sequestering AGE without activation of downstream signaling pathway. (3). The secreted form of (pro)renin receptor (sPRR). The PRR has been implicated in many pathological conditions, particularly in diabetic complications. By binding to both renin or its precursor protein prorenin, the PRR increase renin's intrinsic enzymatic activity leading to increased production of angiotensin and downstream signaling pathways causing vasoconstriction, hypertension, fibrosis, proliferation etc. In addition, (pro)renin binding to PRR also activate downstream signaling events independent of angiotensin production, also leading to fibrotic, proliferative events. The soluble form of PRR may also has beneficial potential by sequestering (pro)renin without activation of deleterious downstream signaling events. (4). Many other neurotrophic factors, such as BDNF (brain-derived neurotrophic factor), could also be used as carrier proteins.

In a particular embodiment, the sequence 18 encoding for the protease cleavage site 26 comprises the following:

(SEQ ID NO. 1)
5' ACC AGA TCT CGC AAG AAG CGC 3'

(SEQ ID NO. 2)
3' TGG TCT AGA GCG TTC TTC GCG 5'

The sequence 18 encoding for the small peptide 28 may be any suitable sequence coding for a small peptide. As used herein, the term "small peptide," it is meant any peptide smaller than 50 amino acid residues, 40 amino acid residues, or 30 amino acid residues. The design of the delivery vector 10 allows the small peptide 28 to be expressed as part of the fusion polypeptide 21. Upon cleavage (after or during secretion), the small peptide 28 will be released extracellularly (or into the circulation if delivered systemically).

The following discussion setting forth an exemplary small peptide 28 for use in the current invention is meant to be exemplary only and it is understood that the invention as described herein is not so limited. In one embodiment, the sequence 18 encoding for the small peptide 28 may be a sequence encoding for the small peptide gp91dsTat, which has shown to be an effective NADPH oxidase inhibitor in vivo in disorders associated with oxidative stress.

Oxidative stress plays a large role in many age-related disorders, e.g., aging, neurodegenerative diseases, cardiovascular diseases (such as atherosclerosis, hypertension, heart failure), and diabetic vascular complications. One of the key contributing enzymes for reactive oxygen species (ROS) is the NADPH oxidase of the NADPH oxidase system. The NADPH oxidase system is one of the only known systems that results in ROS generation not as a byproduct, but as the primary function of the enzyme system. Currently available inhibitors for NADPH oxidase include non-specific (e.g., diphenyleneiodonium) or low affinity (apocynin) inhibitors. One of the more specific and efficacious NADPH oxidase inhibitors developed to date is gp91dsTat. gp91dsTat is a chimeric 18-amino acid peptide that has been shown to interfere with NADPH oxidase assembly and activation. Nine of its amino acids mimic a region of gp1phox (the large catalytic submit; docking sequence: ds) that interacts with the cytoplasmic subunit p47phox and inhibits the assembly of the complex, thereby blocking activation. The next 9 amino acids correspond to a specific sequence in the HIV viral coat, which allows the peptide to be internalized by cells. Despite its believed effectiveness, in vivo application of the gp91dsTat peptide has been limited to date since the small peptide could only be administered intravenously due to its limited bioavailability, relatively short half-life in the cells, and potential immune response over long-term use.

Aspects of the present invention advantageously utilize the developed delivery vector 10 and expression system 12 to deliver a coding sequence to target cells to express the (small) gp91dsTat peptide as part of a much larger construct (the fusion polypeptide 21). Thereafter, the (small) gp91dsTat peptide may be cleaved from the larger fusion polypeptide 21 and secreted from the target cells into the extracellular environment or into the circulation system or lymphatic system. Advantageously, the gp91dsTat peptide may be taken up by cells adjacent to the particular cell from which the gp91dsTat peptide is secreted. In this way, intracellular production of the gp91dsTat peptide overcomes the problem of exogenous peptide delivery and generates sufficient intracellular concentration of the peptide to exhibit inhibition of NADPH oxidase. Accordingly, aspects of the present invention provide a protein expression system that allows the gp91dsTat peptide to be expressed as part of the fusion polypeptide 21 followed by the protease cleavage site 20 to release the bioactive peptide gp91dsTat.

The above-described design for expressing the gp91dsTat peptide is particularly important since many delivery vectors (including AAV vectors) transduce vascular cells poorly. In the present invention, however, the entire coding region, under the control of a promoter, e.g., a CBA promoter, will express a secreted precursor protein (32 kd), and upon secretion and cleavage, releases the inhibitory peptide (gp91dsTat) to be taken up by surrounding cells mediated by the Tat signal. This is a useful feature since the peptide can now diffuse to and enter distant cells that are not usually transduced by AAV vectors, particularly retinal vascular cells. Thus, in one embodiment of the present invention, the delivery vector is utilized to produce gp91dsTat in vivo, and upon secretion from the producing cells, provide uptake of the gp91dsTat by retinal vascular cells.

As mentioned, it will be appreciated to one skilled in the art that a promoter 30 (shown in FIG. 1) may be provided depending on the level and tissue-specific expression desired. The promoter 30 may be a constitutive or inducible promoter, a native or foreign promoter, and/or a natural or synthetic promoter. In one embodiment, the expression system 12 (entire coding sequence) is under the control of a promiscuous and constitutive promoter, e.g., a CMV-β-Actin Promoter, expressed, for example, from a recombinant AAV vector cassette such that the expression system can be used both in vitro (by plasmid transfection experiments) and in vivo (by, for example, AAV-mediated gene delivery). See Lingfei Xu, Thomas Daly, Cuihua Gao, Terence R. Flotte, Sihong Song, Barry J. Byrne, Mark S. Sands, Katherine Parker Ponder. Human Gene Therapy. March 2001, 12(5): 563-573 for a discussion of the use of the CMV-β-Actin Promoter, the entirety of which is incorporated by reference herein.

In addition, the expression system 12 will typically include a sequence encoding for a start codon (e.g., ATG) at the 5' end of the expression gene and a sequence encoding for a stop codon at the 3' end of the expression gene as is known in the art. As is further known in the art, the start codon will encode for methionine at the N terminal of the protein. Further, the sequence encoding for a start codon will encode for UAG, UAA, or UGA.

In accordance with yet another aspect of the present invention, the expression system 12 may include two or more restriction enzyme sites as set forth below to allow for the rapid cloning of any small peptide coding sequences of interest by designing oligo-nucleotides flanked by these two restriction enzyme sites. In one embodiment, for example, the sequence 18 encoding for the small peptide 28 may be flanked by two restriction enzyme sites such that new peptide-coding oligonucleotides may easily be cloned into the fusion polypeptide 21 with minimal manipulation, allowing a large number of new and bioactive small peptides to be tested easily. In a particular embodiment, the sequence 18 encoding for the protease cleavage site 26 comprises the following sequence:

(SEQ ID NO. 1)
5' ACC A↓GA TCT CGC AAG AAG CGC 3'

(SEQ ID NO. 2)
3' TGG TCT AG↑A GCG TTC TTC GCG 5'

(SEQ ID NO. 3)
Thr Arg Ser Arg Lys Lys Arg

In this embodiment, as shown, the above-underlined portion of the sequence 18 defines a first restriction site that may be recognized by a suitable enzyme, such as a BglII enzyme, and cleaved by the enzyme at the positions indicated by the arrows. Alternatively, any other suitable restriction enzyme site and restriction enzyme known in the art may be utilized, including, but not limited to, an XhoI site and an XhoI enzyme. A further (second) restriction enzyme site may be provided, for example, after the end of the stop codon having the following sequence.

C↓TCGA G

G AGCT↑C

As with the first restriction site, the ↓ and ↑ symbols indicate positions where the restriction site may be cleaved by a suitable enzyme, such as a BglII enzyme, XhoI enzyme, or the like. Alternatively, any other suitable restriction sites may be added to the expression system 12. It is understood to one skilled in the art if a portion of the sequence 18 encoding for the protease cleavage site 26 is removed by the restriction enzymes, the same sequence may be added to the "new replacement" small peptide to be inserted back into the expression system 12.

The following examples further describe aspects of the present invention, but are not intended to be limiting.

Example 1

Figures 3A, 3B, 3C, 3D:
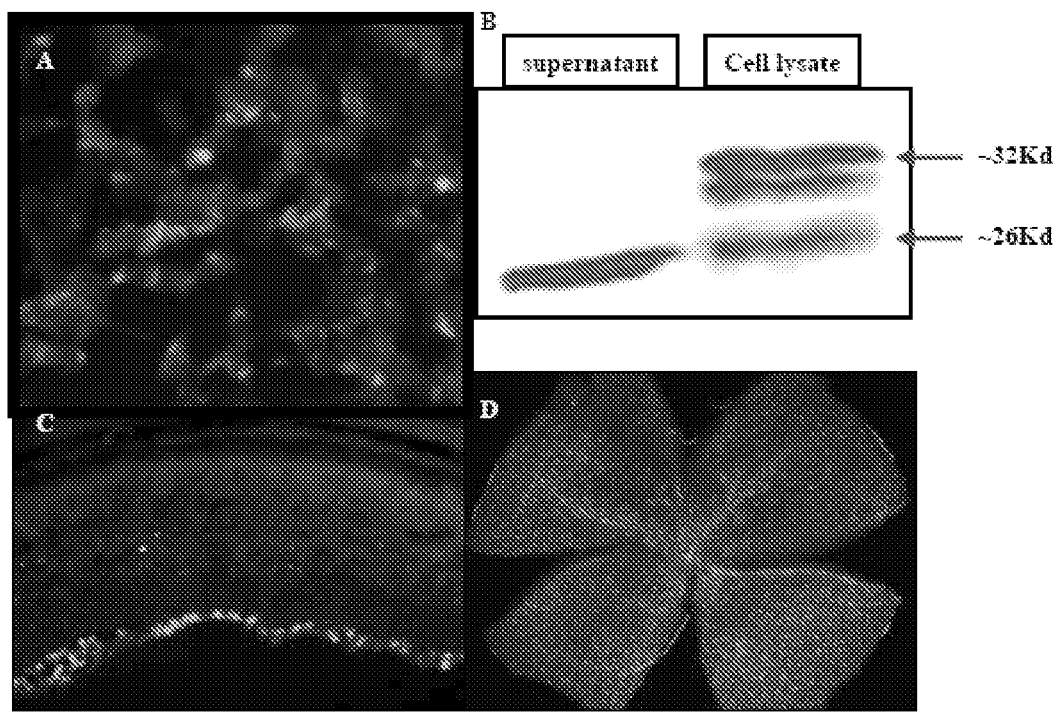
FIGS. 3A-3D illustrate the in vitro and in vivo characterization of the peptide expression system.

FIGS. 3A-3D illustrate the in vitro and in vivo characterization of peptide expression system embodiment. In FIG. 3A, there is shown the in vitro transfection of HEK293 cells with the plasmid (sGFP-FC-gp91dsTat-UF11). (sGFP=GFP protein; FC=furin cleavage site; gp91dsTat=small peptide; UF11=vector design). GFP is expressed and is associated with the cell membrane and may be used to monitor the expression of the subject small peptide. In FIG. 3B, there is shown the Western blotting detection of GFP in the supernatant and cell lysate isolated from HEK293 cells transfected with the plasmid. In the cell lysate, full-length, intermediate processed and fully processed bands can be detected, whereas in the supernatant only processed GFP is detectable. In FIGS. 3C and 3D, there is shown GFP expression, which is detectable in retina injected with AAV2-sGFP-FC-gp91dsTat on section (C) and retinal wholemount (D).

Example 2

Figure 4:
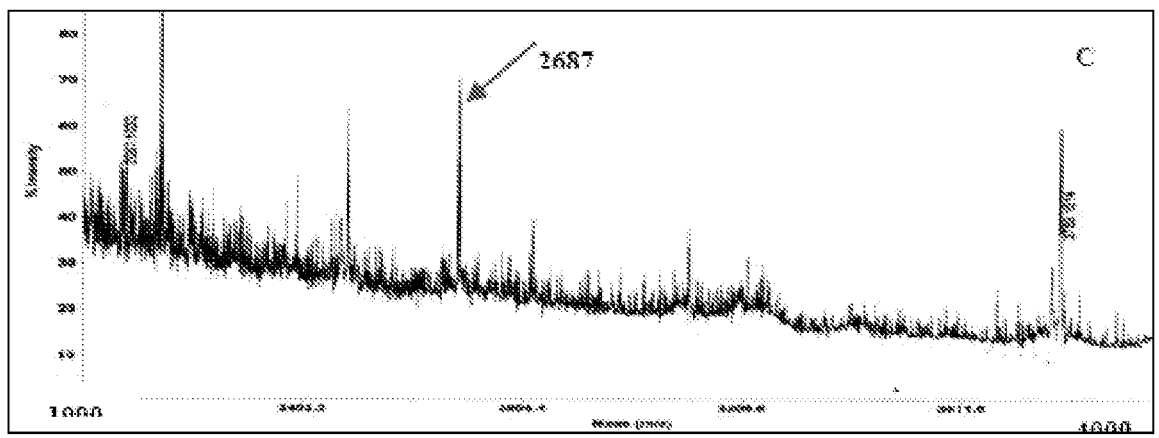
FIG. 4 is a mass spectrum confirming the presence of the cleaved gp91dsTat peptide.

The peptide expressed from the expression system (fusion construct) is active after cleavage. As shown by FIG. 4, the cleaved gp91dsTat peptide is biologically active and detectable by mass spectrometry. In particular, FIG. 4 shows gp91dsTat from supernatant concentrated from HEK293 cells transfected with the sGFP-FC-gp91dsTat-UF11 plasmid DNA is detected by mass spectrometry. The same peak was absent in control plasmid (GFP-UF11) transfected or non-transfected supernatant samples (data not shown).

Example 3

Figure 5:
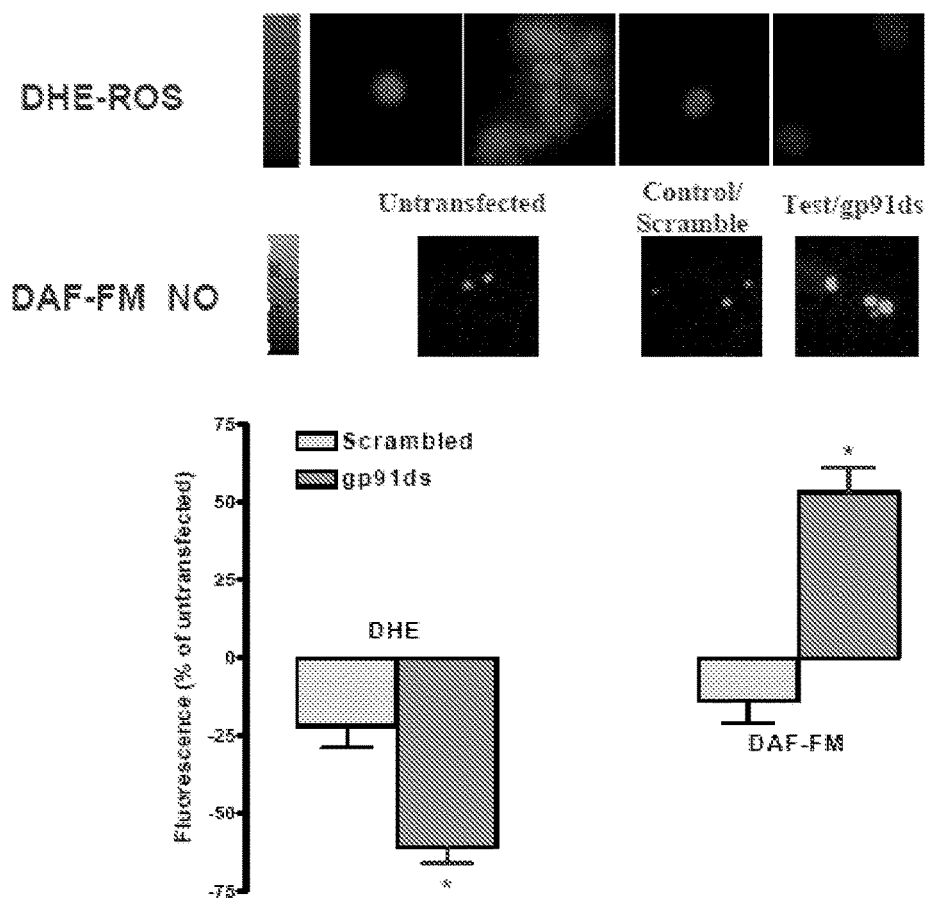
FIG. 5 shows the treatment of diabetic CD34+ cells with gp91ds-Tat decreases ROS production and increases NO release.

This Example shows the efficacy of gp91dsTat expressed by an expression system in accordance with an aspect of the present invention. As shown in FIG. 5, the supernatant concentrated from sGFP-FC-gp91dsTat-UF11 transfected HEK293 cells inhibited ROS (detected by dihydro ethidium staining—DHE) and stimulated NO production (detected by DAF-FM staining) in vitro.

More specifically, as shown in FIG. 5, treatment with gp91ds-Tat was shown to decrease ROS production and increases NO release in diabetic CD34+ cells. In the upper portion of the figure, imaging of ROS by dihydroethidine (DHE, top panel) and NO production by DAF-FM (bottom panel) is shown. Shown on left were corresponding color scales. In the graph on the lower portion of the FIG. 5, DHE and DAF-FM fluorescence in cells treated with gp91ds-Tat or its inactive/scrambled form gp91scr-Tat is shown as a percentage of untransfected cells. Treatment with gp91ds-Tat decreased basal ROS production significantly ($P<0.01$) and increased NO production ($P<0.01$) compared to that treated with a control.

Example 4

Figure 6:
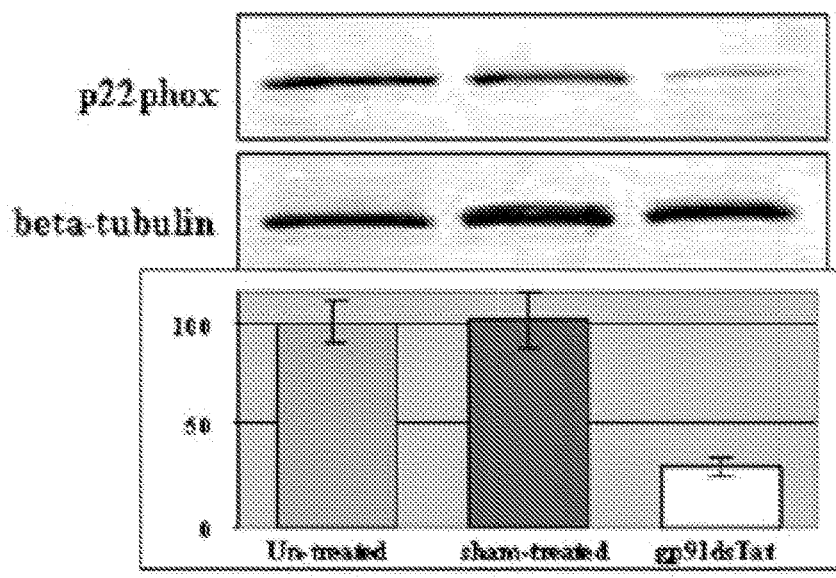
FIG. 6 shows that gp91dsTat expressed as part of a fusion polypeptide also reduced p22phox, the small catalytic subunit of NADPH oxidase, in diabetic retina.

As shown in FIG. 6, gp91dsTat expressed as part of a fusion polypeptide as described herein also reduced p22phox, the small catalytic subunit of NADPH oxidase, in diabetic retinal cells. As shown, injection of an AAV2-sGFP-FC-gp91dsTat vector into diabetic eNOS KO mouse eyes resulted in reduction in the level of p22phox protein. Lane 1: un-injected. Lane2: control AAV2-GFP-UF11 injected. Lane 3: AAV2-sGFP-FC-gp91dsTat injected. Thus, the vector design allows efficient expression and secretion of the GFP-FC-gp91dsTat fusion polypeptide. When the peptide portion (gp91dsTat) is cleaved, the peptide is relatively stable and is able to be detected and is biologically active both in vitro and in vivo.

Example 5

Figure 7:
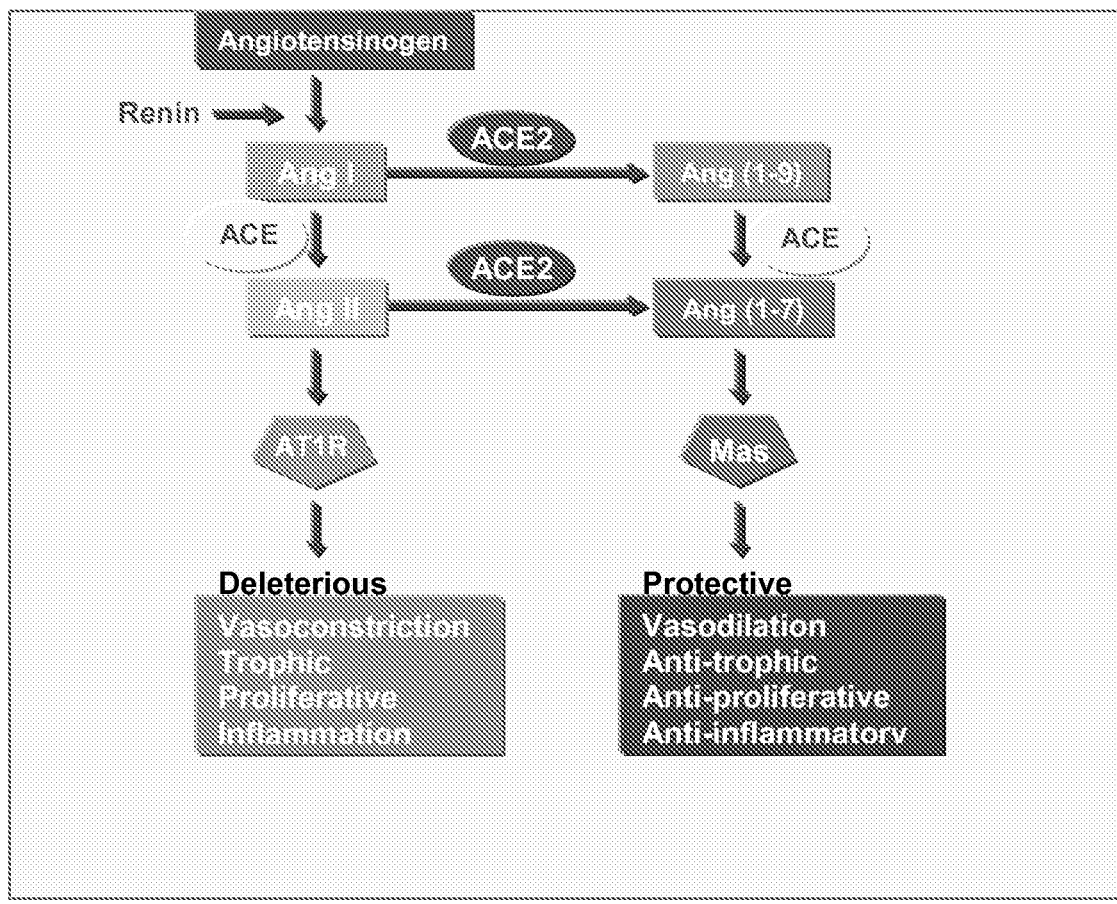
FIG. 7 Renin Angiotensin System (RAS). Ang I: angiotensin I; Ang (1-9): Angiotensin (1-9); Ang II: Angiotensin II; Ang (1-7): Angiotensin (1-7); ACE: angiotensin converting enzyme; ACE2: angiotensin converting enzyme 2; AT1R: angiotensin type 1 receptor.

Ang1-7 Peptide Expression System.
Biological Function of Ang1-7 Peptide
Angiotensin (1-7) (Ang 1-7) is a naturally occurring peptide hormone in the renin angiotensin system (RAS), which is a major regulator of cardiovascular system. Ang 1-7 is normally formed from Angiotensin II (Ang II) by angiotensin converting enzyme 2 (ACE2) [1], or by another prolyl endopeptidase, prolylcarboxypeptidase [2]. It can also be formed from Angiotensin I (Ang I) by endopeptidases, including neutral endopepdiase 24.11 (NEP), and prolylendopeptidase or indirectly through ACE2-mediated formation of Ang (1-9) [3], which is subsequently metabolized to Ang1-7 by angiotensin converting enzyme (ACE) or NEP [4] (see diagram shown in FIG. 7).

Since the first discovery of Ang 1-7 as a potent peptide opposing the deleterious effects of Ang II two decades ago [5, 6], overwhelming evidence has demonstrated its beneficial effects in cardiovascular and renal pathology (recently reviewed in [7-9]). Ang 1-7 has been shown to possess anti-hypertensive, antihypertrophic, antifibrotic, anti-inflammatory, and anti-thrombotic properties, all of which may prove beneficial in clinical settings. It may be used to treat cardiac hypertrophy, heart failure, hypertension, kidney disease, diabetic complications, preeclampsia, and cancer. In fact, Ang 1-7 was examined in a Phase I/II clinical trial to determine its effectiveness and optimal dose against chemotherapy-induced cytopenias in breast cancer patients by repeated subcutaneous administration and was found to attenuate cytopenias associated with chemotherapy without any hematologic toxicity [10]. However, for treating cardiovascular diseases, this approach does not represent a suitable tactic, due its unfavorable pharmacological properties (poor bioavailability, very short half life), especially if when involving costly chronic treatment.

We have designed an expression vector to allow the Ang 1-7 peptide to be secreted continuously from cells by means of gene delivery. Because short peptides are difficult to express in mammalian cells, we have designed a peptide expression system (see previous Invention Disclosure UF #-13020) that allows the peptide to be expressed as the product of large precursor protein followed by specific protease cleavage to release the bioactive peptide Ang1-7.

Example 6

Figure 8:
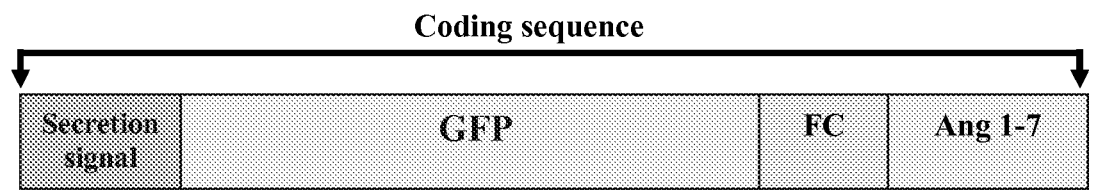
FIG. 8 shows a diagram of a genetic construct embodiment.

The Ang 1-7 Peptide Expression Vector:
As shown in FIG. 8, the expression vector contains the following elements: The coding sequence for this expression system contains the following elements:

(1). A secretion signal. The secretion signal allows the encoded protein to secrete extracellularly (or into the circulation if delivered systemically), thus exerting the biological function of the peptide not only in the cells harboring the expression system, but also on distant cells. The secretion signal contains 21 amino acid residues derived from IgK signal sequence (Met-Glu-Thr-Asp-Thr-Leu-Leu-Leu-Trp-Val-Leu-Leu-Leu-Trp-Val-Pro-Gly-Ser-Thr-Gly-Asp) (SEQ ID NO. 4).

(2). A coding sequence for GFP. The GFP, green fluorescent protein, can serve both as a scaffold and reporter protein to monitor the expression level, cell/tissue and intracellular distribution of the expressed protein. This protein acts merely as a scaffold or carrier. In other embodiments and for clinical use it may be replaced with a naturally occurring human protein such as serum albumin. For preclinical testing in animals we prefer the fluorescent protein because it is easy to detect.

(3). A sequence-specific protease cleavage site. This cleavage site allows the peptide portion of the precursor protein to be cleaved precisely following synthesis and secretion. We have designed the cleavage sequence based on a ubiquitous protease, furin, which is present both in the Golgi network, as well as extracellular space of virtually all mammalian cell types. An artificial furin cleavage (FC) site was designed after careful comparison of available natural protein substrates of furin protease, with enhanced affinity for furin cleavage. The furin cleavage sites contain the following amino acid sequence: Thr-Arg-Ser-Arg-Lys-Lys-Arg. The precise cleavage takes place after the last Arg residue.

The DNA sequence encoding the furin protease cleavage site contains a built-in restriction site BlgII (highlighted in sequence below the arrow pointing the cleavage site by this enzyme):

```
                                           (SEQ ID NO. 1)
5' ACC A↓GA TCT CGC AAG AAG CGC 3'

(SEQ ID NO. 2)
3' TGG TCT AG↑A GCG TTC TTC GCG 5'
```

This furin protease coding sequence is immediately followed by peptide coding sequence which is followed by a stop codon. Another restriction site is incorporated at the end the stop codon-XhoI site:

G↓TCGAG
GAGCT↑C

This feature allows rapid cloning of any peptide coding sequence of interest by designing oligo-nucleotides flanked by these two restriction sites.

Example 7

Ang 1-7 Peptide Coding Sequence.

Asp-Arg-Val-Tyr-Ile-His-Pro (SEQ ID NO. 5) This design of the expression system allows the Ang 1-7 peptide to be expressed as part of the fusion protein, and upon cleavage (after or during secretion), the peptide will be released extracellularly (or into the circulation if delivered systemically). The entire coding sequence is under the control of a promiscuous promoter, the chicken β-actin/CMV enhancer promoter (CBA), expressed from a recombinant AAV vector cassette, so that the expression system can be used both in vitro (by plasmid transfection experiments) and in vivo (by AAV-mediated gene delivery). The precursor (fusion protein) is expressed both in vitro and in vivo, and the peptide is cleaved precisely at the site as expected. Codons from the Ang 1-7 amino acids were employed that correspond to highly expressed proteins in human (GAC CGC GTG TAC ATC CAC CCC) (SEQ ID NO. 6).

Figure 9:
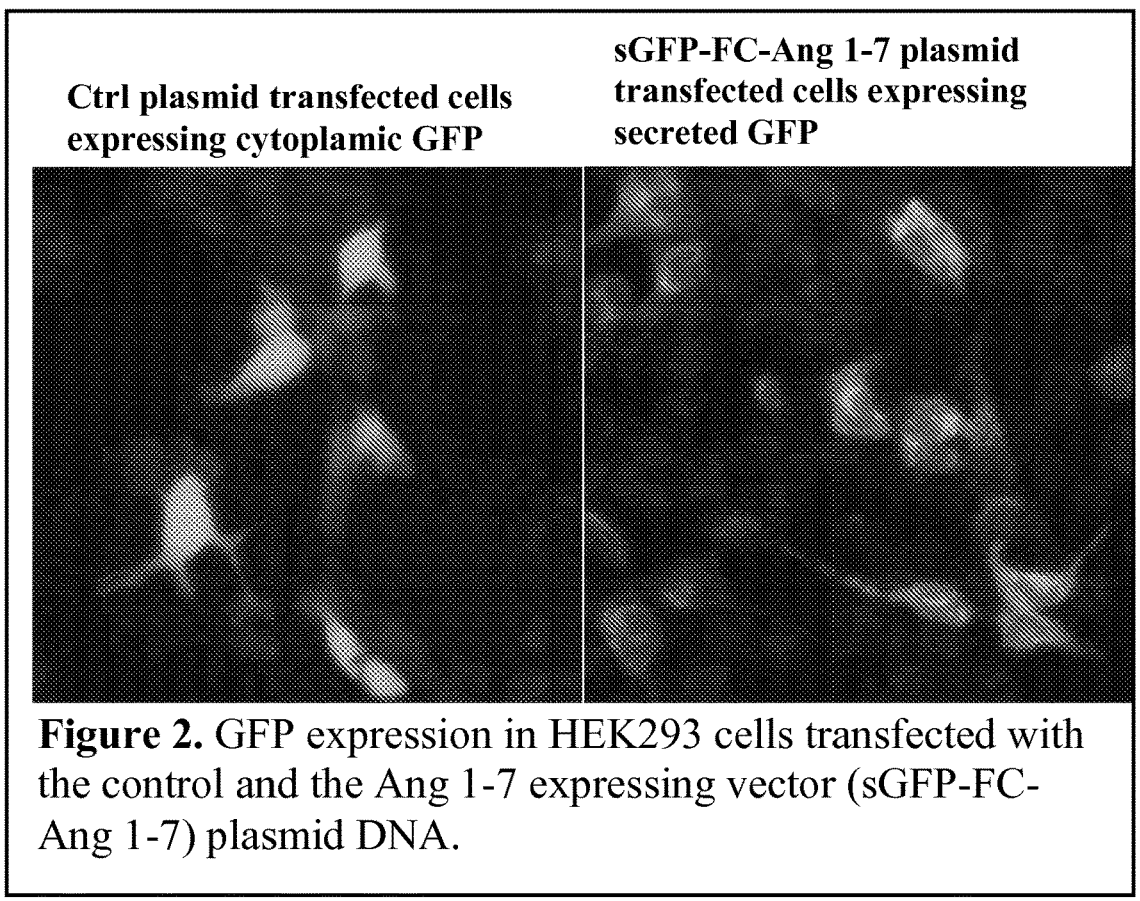
FIG. 9 GFP expression in HEK293 cells transfected with the control and the Ang 1-7 expressing vector (sGFP-FC-Ang 1-7) plasmid DNA.
Figure 10:
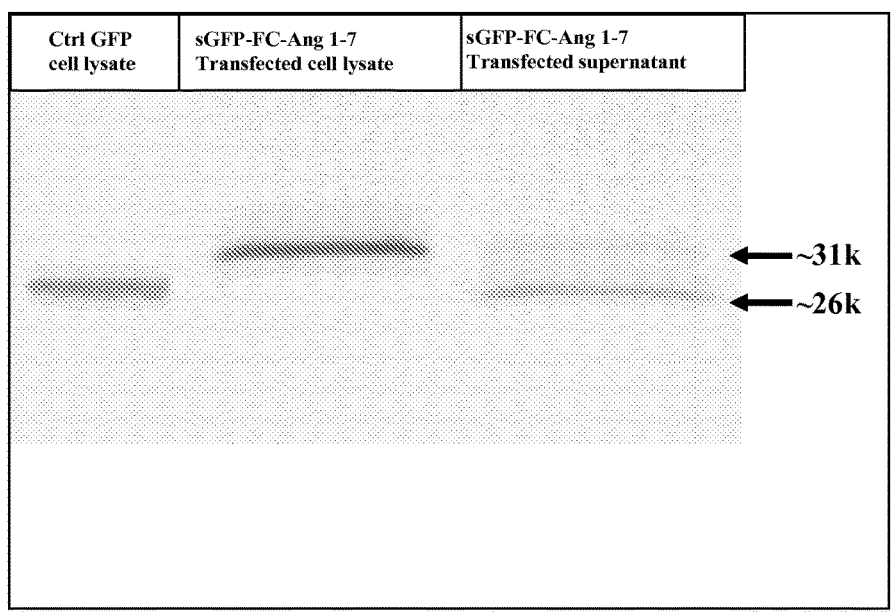
FIG. 10 Western blotting analysis of GFP expression in HEK293 cells transfected with the control and the Ang 1-7 expressing vector (sGFP-FC-Ang 1-7) plasmid DNA.
Figure 11:
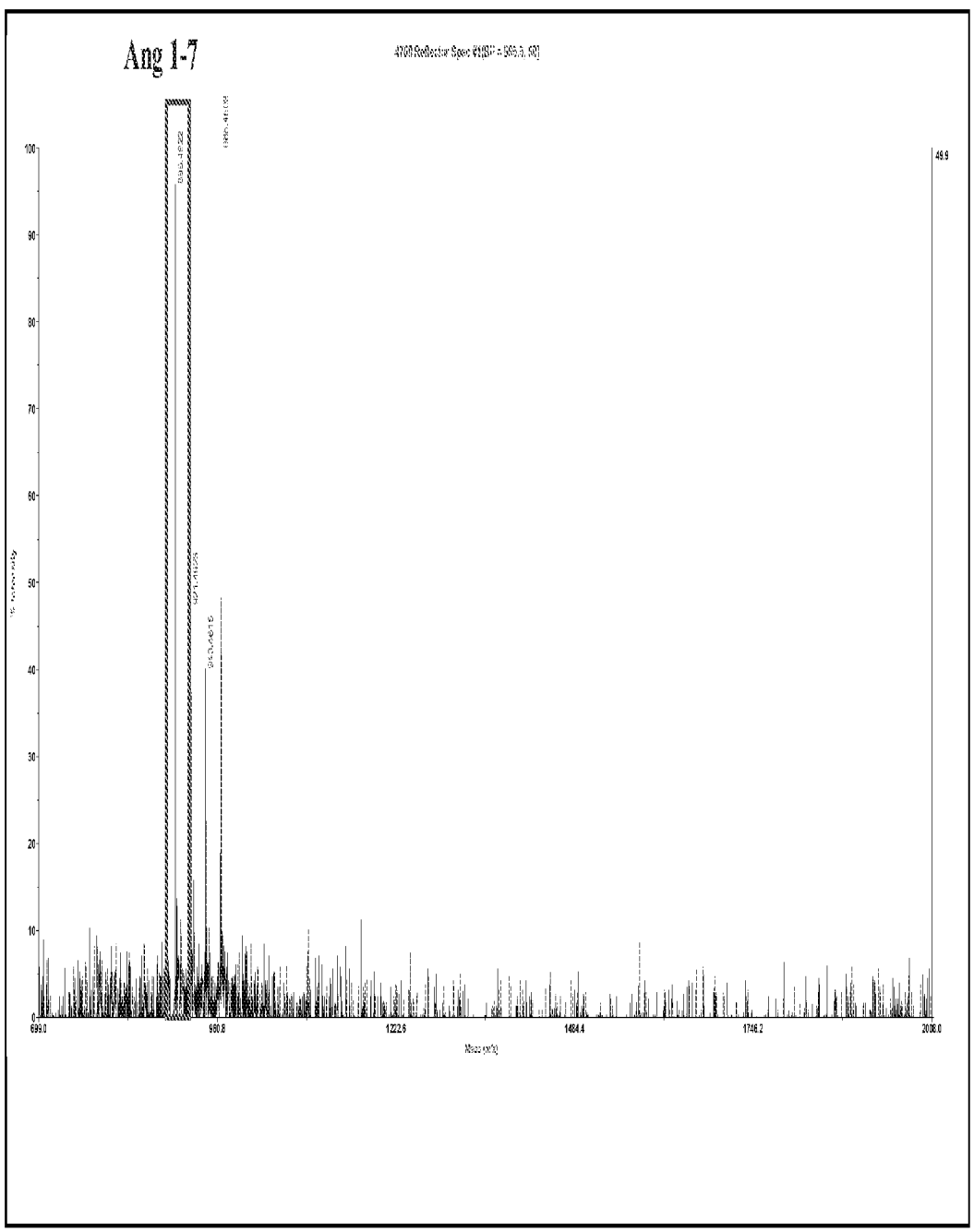
FIG. 11 Mass spectrometry analysis of Ang 1-7 peptide in supernatant samples of HEK293 cells transfected with the Ang 1-7 expressing vector (sGFP-FC-Ang 1-7) plasmid DNA.

As shown in FIG. 9, in cultured HEK293 cells transfected with a control plasmid expressing the cytoplasmic GFP, the GFP is accumulated in cytoplasm, whereas in cells transfected with the plasmid sGFP-FC-Ang1-7, the protein is targeted to endoplasmic reticulum (ER) and Golgi for secretion. On Western blot probed with an anti-GFP antibody (shown in FIG. 10), proteins isolated from cell lysates contained a single protein band with molecular weight ~31 kd, as predicted for the precursor (fusion protein), but contained two protein bands (31 kd and a 26 kd), indicating that the secreted protein is cleaved at the furin cleavage site as predicted. The Ang 1-7 peptide is detectable in supernatant isolated from cells transfected with sGFP-FC-Ang 1-7 plasmid (shown in FIG. 11), but not detectable in samples isolated from un-transfected cells, or cells transfected with the control plasmid expressing the cytoplasmic GFP (data not shown).

Figure 12:
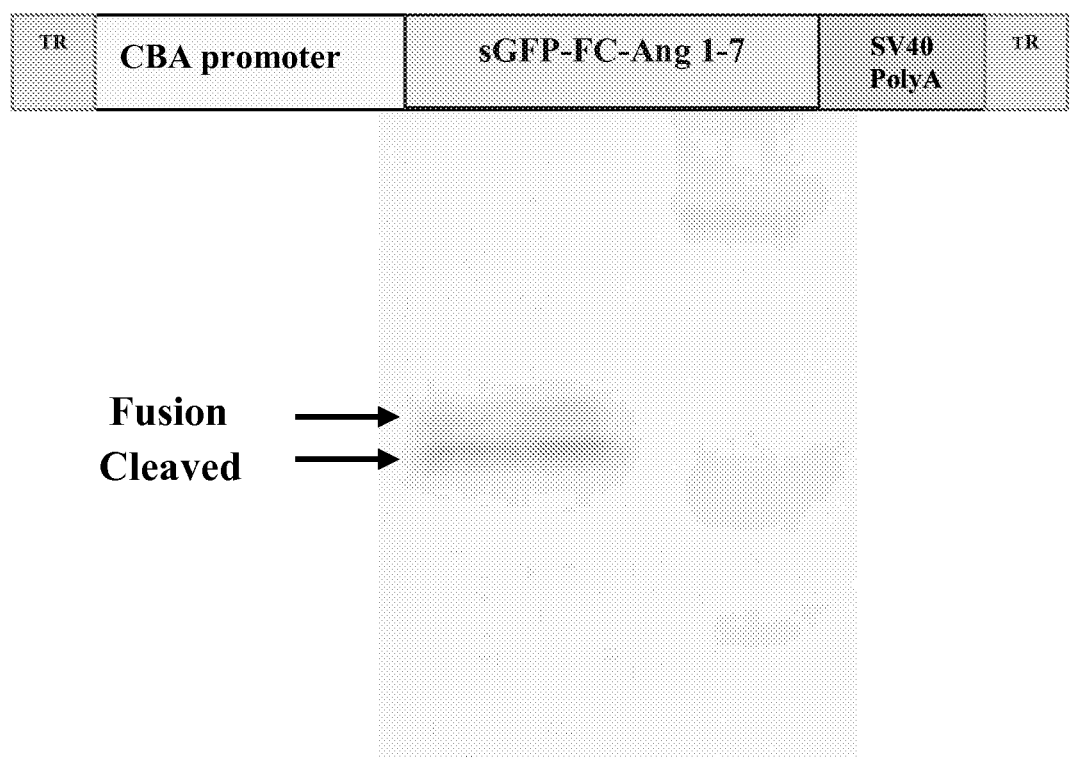
FIG. 12 Western blotting analysis of GFP expression in retinas received ocular injection of AAV vector containing the sGFP-FC-Ang 1-7 expression cassette (shown in diagram on the top).
Figure 13:
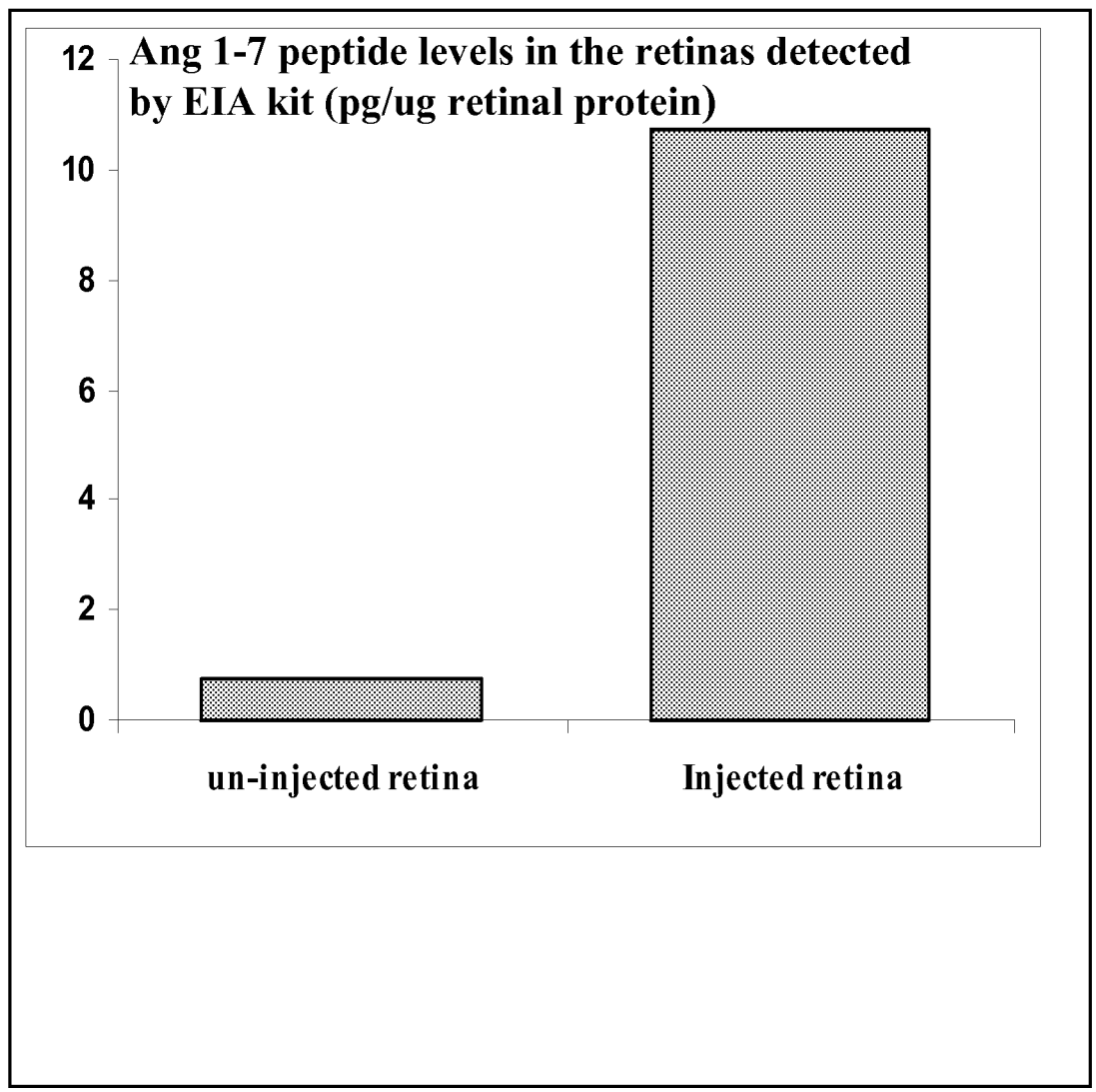
FIG. 13 Ang 1-7 peptide Enzyme Immunoassay (EIA) analysis of retinal protein extracts in eyes received ocular injection of AAV vector containing the sGFP-FC-Ang 1-7 expression cassette.

In protein extracts isolated from retinas received injection of AAV vector expressing sGFP-FC-Ang 1-7, both fusion and cleaved GFP can be detected as expected (shown in FIG. 12). There is more than 10-fold increase in Ang 1-7 peptide level detected by using an Ang 1-7 specific EIA kit (Bachem SAN CARLOS, Calif.) (shown in FIG. 13) in retinas received injection of AAV vector expressing sGFP-FC-Ang 1-7. Thus this vector design allows efficient expression and secretion of GFP-FC-Ang 1-7 fusion protein, with the Ang 1-7 peptide portion cleaved and this peptide can be detected both in vitro and in vivo.

Example 8

Figure 14:
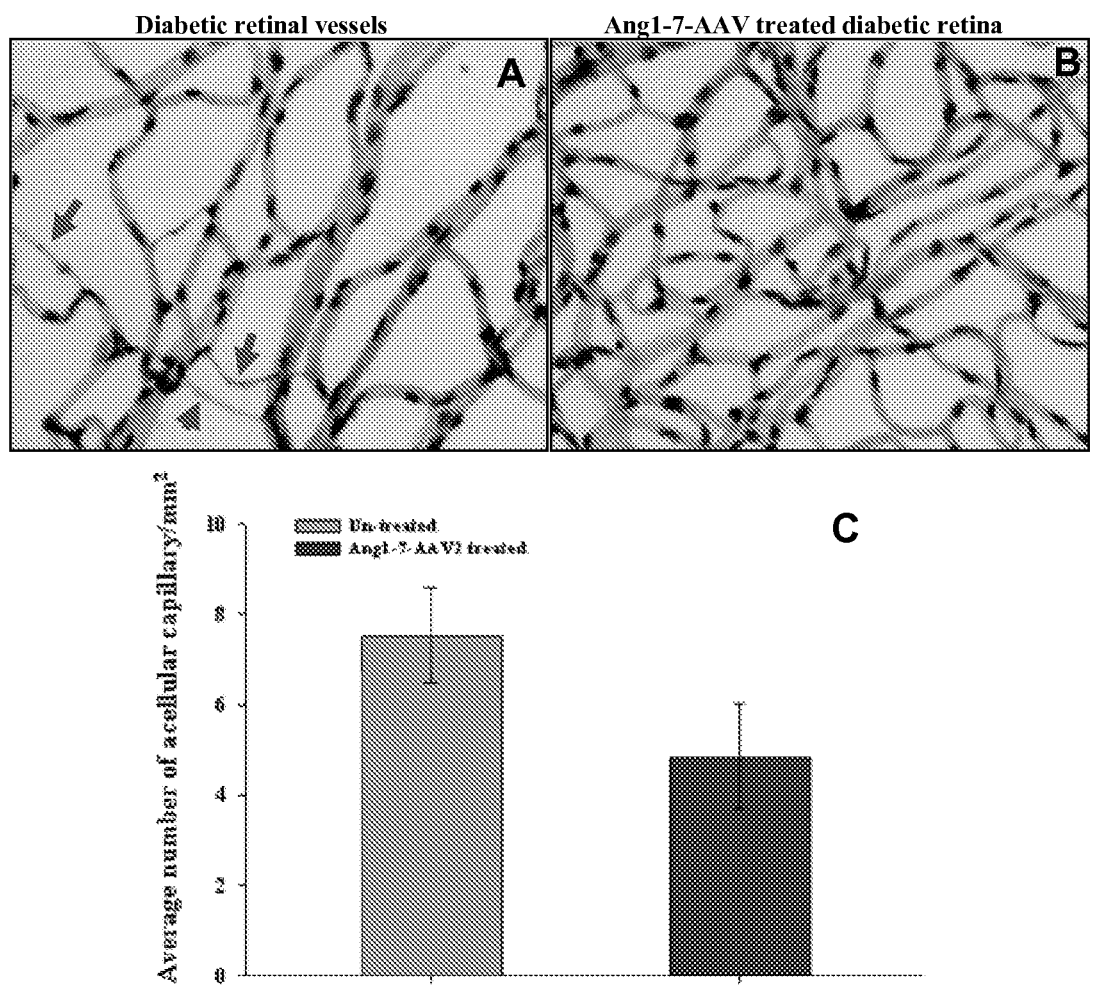
FIG. 14 Trypsin-digested retinal vascular preparation from untreated eye (A), Ang1-7-AAV vector treated (B), and the acellular capillary cell counting (#/mm2) in treated and untreated eyes (C). Arrows point the "ghost" acellular capillaries.

Ang1-7 Peptide Expressed from AAV Vector has Protective Role in Animal Model of Diabetic Retinopathy Diabetic retinopathy (DR) is the most common form of diabetic vascular complications, and the leading cause of severe vision loss in people under age of sixty. Increasing evidence indicates that the renin-angiotensin-system (RAS) in the eye plays a significant local role in retinal vascular dysfunction in DR. We evaluated the effect of Ang1-7 expressing AAV vector in animal models of DR. The vector was injected into intravitreal cavity of one eye of streptozocin (STZ) induced diabetic animals (both mice and rats). The other eye served as a control. As shown in FIG. 14, treatment with Ang1-7 peptide expressing AAV vector resulted in a significant reduction in retinal vascular permeability and endothelial cell loss.

Example 9

Angiotensin II (AngII) Peptide Expression System

Figure 15:
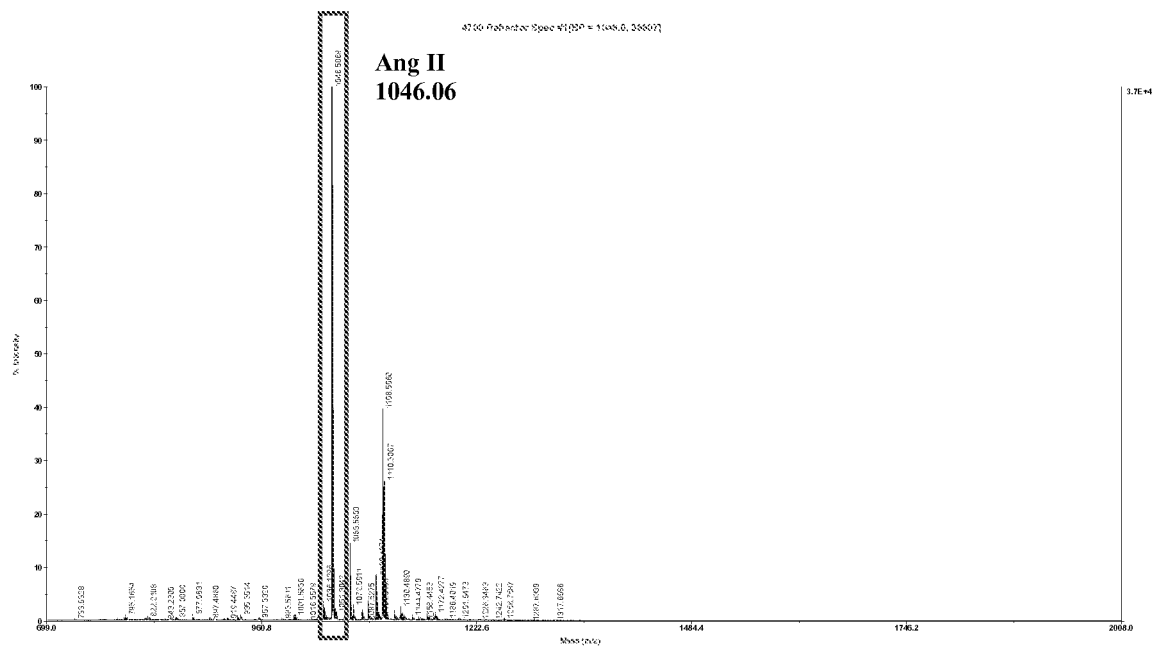
FIG. 15 Mass spec analysis of supernatant collected from cultured HEK293 cells transfected with AngII expression vector.
Figure 16:
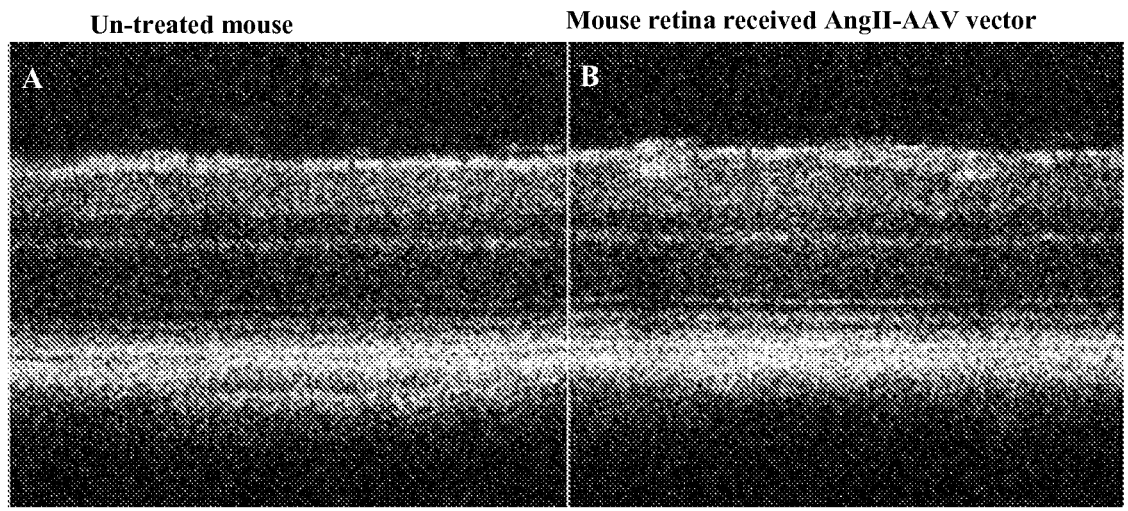
FIG. 16 Optical Coherent Tomograph (OCT) imaging of un-treated (A) and AngII-AAV vector treated (B) mouse retinas. AngII expression from AAV vector caused increased vascular permeability, i.e. edema, thus increased inner retinal thickness.

Similar to that described in Examples 5-8, an expression vector for Angiotension II peptide (DRVYIHPF (SEQ ID NO. 7), MW=1046.06) was also constructed, and characterized using the methods for Ang 1-7 peptide. Analysis of supernatant collected from cultured HEK293 indicated that the peptide is secreted and can be detected as single peak by mass spec (FIG. 15). Eyes received intraocular injection of AngII-AAV vector show increased retinal vascular leakage, and can be detected by Optical Coherent Tomograph (OCT) imaging (FIG. 16). Treatment with this vector also increased inflammatory cell infiltration in the eye (data not shown), indicating that the AngII peptide expressed from this vector is biologically active.

Example 10

AAT Carrier Protein Construct

In Examples 1-4, GFP was used with a fusion protein construct with subsequent cleavage to release peptide. The advantage using GFP as a fusion carrier protein is that the level of protein expression and their cellular distribution can be easily visualized and quantitatively measured. However as therapeutic candidate for clinical applications, carrier proteins with human origin must be used. The carrier proteins should be either neutral, with no known adverse biological activity on its own, or beneficial/protective when over-expressed with no or very minimal immunogenecity. One candidate of the former is the albumin protein, which is abundantly present in the circulation. A candidate of later is the alpha-1 antitrypsin (AAT).

AAT is a 52 kDa glycoprotein containing 418 amino acid, that is primarily synthesized and secreted by the hepatocytes in the liver [11]. AAT functions as a serine proteinase inhibitor secreted from hepatocytes and traversed to the lung, where is protects elastin from degradation by neutrophil elastase. It is also actively transcribed and secreted in smaller amount by cells including neutrophils, mononuclear phagoctes, enterocytes [12] and human respiratory epithelial cells [13]. It is present in all tissues of the body with its primary role being to inhibit the enzyme neurtrophil elastase [14]. It also inhibits to a much lesser degree trypsin, chymotrypsin, cathepsin G, plasmin, thrombin, tissue kallikrein, factor Xa, plasminogen, and proteinase 3 [15].

Several features of AAT render it a favorable candidate as a carrier gene/protein:

(1). AAT is abundant protein in serum and is present in all tissues. Serum AAT concentration below 0.5g1 (11 uM) can cause panacinar emphysema due to destruction of the lung elastin fibers. AAT deficiency is the second-most common lung disease and account for 3% of all early deaths due to obstructive pulmonary disease [16]. Augmentation therapy either with clinical grade protein and AAV-vector mediated gene delivery of human AAT (hAAT) gene is well tolerated. Given the limited treatment options for AAT deficiency, gene therapy represents a promising treatment for long-term correction of this metabolic disorder. Administration of vectors such as AAV, and adenovirus and helper-dependent adenovirus to the liver or muscle achieved stable therapeutic expression of human AAT in small and large animal models [17-21].

(2). Human AAT protein has low immunogenecity and may have tolerogenic immune properties. Neither adverse events nor clinically relevant neutralizing antibodies against exogenously administered AAT have been observed in routinely in AAT-deficient patients receiving human AAT, AAT has long been considered a remarkably safe drug [22, 23]. AAV vector encoding human AAT is currently being pursued in human clinical trials [22-24].

Figure 17:
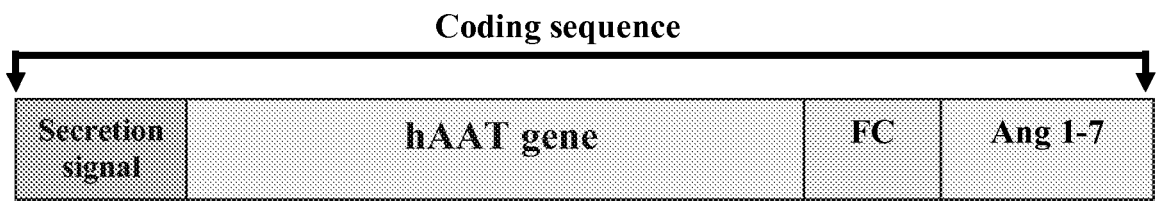
FIG. 17 shows a genetic construct embodiment.

(3). AAT has other beneficial functions in addition to elstase inhibition. It has pro-survival function by inhibiting apoptosis, modulating immune responses, reduce inflammations [25-27]. In addition, AAT treatment also provides a pronounced therapeutic benefit in settings potentially meaningful to those with type 1 diabetes (T1D). Specifically, it was shown that early gene delivery of human AAT to NOD mice prevents T1D development, reduces the levels of insulin autoantibodies and attenuates the development of insulitis [28, 29] and prolong islet allograft survival in mice [30]. We have modified the peptide expression vector using human AAT as a part of fusion construct as shown in FIG. 17. The therapeutic potential of this construct is currently being evaluated in several disease models including diabetes and its complications.

Example 11

Figure 18:
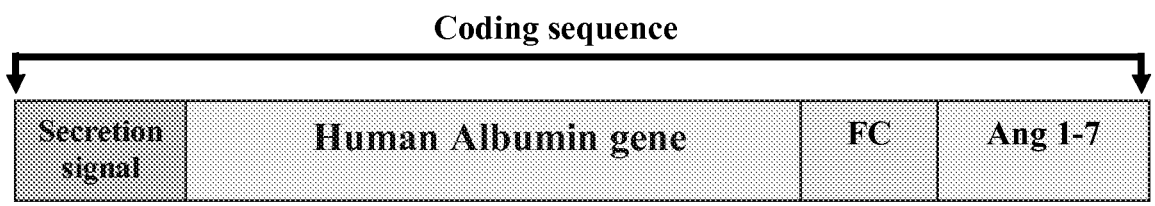
FIG. 18 shows a genetic construct embodiment

Human Albumin as a carrier protein. As a neutral carrier protein, human albumin is also a good candidate. The construct shown in FIG. 18 is expressed according to the teachings herein.

In reviewing the detailed disclosure which follows, and the specification more generally, it should be borne in mind that all patents, patent applications, patent publications, technical publications, scientific publications, and other references referenced herein are hereby incorporated by reference to the extent not inconsistent with the teachings herein.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

LITERATURE CITED

1. Santos, R. A., M. J. Campagnole-Santos, and S. P. Andrade, *Angiotensin-(1-7): an update*. Regul Pept, 2000. 91(1-3): p. 45-62.
2. Tan, F., et al., *Sequencing and cloning of human prolyl-carboxypeptidase (angiotensinase C). Similarity to both serine carboxypeptidase and prolylendopeptidase families*. J Biol Chem, 1993. 268(22): p. 16631-8.
3. Donoghue, M., et al., *A novel angiotensin-converting enzyme-related carboxypeptidase (ACE2) converts angiotensin I to angiotensin 1-9*. Circ Res, 2000. 87(5): p. E1-9.
4. Rice, G. I., et al., *Evaluation of angiotensin-converting enzyme (ACE), its homologue ACE2 and neprilysin in angiotensin peptide metabolism*. Biochem J, 2004. 383(Pt 1): p. 45-51.
5. Campagnole-Santos, M. J., et al., *Cardiovascular effects of angiotensin-(1-7) injected into the dorsal medulla of rats*. Am J Physiol, 1989. 257(1 Pt 2): p. H324-9.
6. Schiavone, M. T., et al., *Release of vasopressin from the rat hypothalamo-neurohypophysial system by angiotensin-(1-7) heptapeptide*. Proc Natl Acad Sci USA, 1988. 85(11): p. 4095-8.
7. Iusuf, D., et al., *Angiotensin-(1-7): pharmacological properties and pharmacotherapeutic perspectives*. Eur J Pharmacol, 2008. 585(2-3): p. 303-12.
8. Trask, A. J. and C. M. Ferrario, *Angiotensin-(1-7): pharmacology and new perspectives in cardiovascular treatments*. Cardiovasc Drug Rev, 2007. 25(2): p. 162-74.
9. Simoes e Silva, A. C., et al., *The therapeutic potential of Angiotensin-(1-7) as a novel Renin-Angiotensin System mediator*. Mini Rev Med Chem, 2006. 6(5): p. 603-9.
10. Rodgers, K. E., J. Oliver, and G. S. diZerega, *Phase I/II dose escalation study of angiotensin 1-7 [A(1-7)] administered before and after chemotherapy in patients with* newly diagnosed breast cancer. Cancer Chemother Pharmacol, 2006. 57(5): p. 559-68.
11. Rogers, J., et al., *The isolation of a clone for human alpha 1-antitrypsin and the detection of alpha 1-antitrypsin in mRNA from liver and leukocytes.* Biochem Biophys Res Commun, 1983. 116(2): p. 375-82.
12. Molmenti, E. P., D. H. Perlmutter, and D. C. Rubin, *Cell-specific expression of alpha 1-antitrypsin in human intestinal epithelium.* J Clin Invest, 1993. 92(4): p. 2022-34.
13. Hu, C. and D. H. Perlmutter, *Cell-specific involvement of HNF-1 beta in alpha(1)-antitrypsin gene expression in human respiratory epithelial cells.* Am J Physiol Lung Cell Mol Physiol, 2002. 282(4): p. L757-65.
14. Travis, J., et al., *Isolation and properties of recombinant DNA produced variants of human alpha 1-proteinase inhibitor.* J Biol Chem, 1985. 260(7): p. 4384-9.
15. Crystal, R. G., et al., *The alpha 1-antitrypsin gene and its mutations. Clinical consequences and strategies for therapy.* Chest, 1989. 95(1): p. 196-208.
16. Kelly, E., et al., *Alpha-1 antitrypsin deficiency.* Respir Med.
17. Song, S., et al., *Sustained secretion of human alpha-1-antitrypsin from murine muscle transduced with adeno-associated virus vectors.* Proc Natl Acad Sci USA, 1998. 95(24): p. 14384-8.
18. Cerullo, V., et al., *Antigen-specific tolerance of human alpha1-antitrypsin induced by helper-dependent adenovirus.* Hum Gene Ther, 2007. 18(12): p. 1215-24.
19. Kay, M. A., et al., *Therapeutic serum concentrations of human alpha-1-antitrypsin after adenoviral-mediated gene transfer into mouse hepatocytes.* Hepatology, 1995. 21(3): p. 815-9.
20. Song, S., et al., *Stable therapeutic serum levels of human alpha-1 antitrypsin (AAT) after portal vein injection of recombinant adeno-associated virus (rAAV) vectors.* Gene Ther, 2001. 8(17): p. 1299-306.
21. Song, S., et al., *Intramuscular administration of recombinant adeno-associated virus 2 alpha-1 antitrypsin (rAAV-SERPINA1) vectors in a nonhuman primate model: safety and immunologic aspects.* Mol Ther, 2002. 6(3): p. 329-35.
22. Brantly, M. L., et al., *Phase I trial of intramuscular injection of a recombinant adeno-associated virus serotype 2 alpha1-antitrypsin (AAT) vector in AAT-deficient adults.* Hum Gene Ther, 2006. 17(12): p. 1177-86.
23. Flotte, T. R., et al., *Phase I trial of intramuscular injection of a recombinant adeno-associated virus alpha 1-antitrypsin (rAAV2-CB-hAAT) gene vector to AAT-deficient adults.* Hum Gene Ther, 2004. 15(1): p. 93-128.
24. Brantly, M. L., et al., *Sustained transgene expression despite T lymphocyte responses in a clinical trial of rAAV1-AAT gene therapy.* Proc Natl Acad Sci USA, 2009. 106(38): p. 16363-8.
25. Zhang, B., et al., *Alpha1-antitrypsin protects beta-cells from apoptosis.* Diabetes, 2007. 56(5): p. 1316-23.
26. Petrache, I., et al., *alpha-1 antitrypsin inhibits caspase-3 activity, preventing lung endothelial cell apoptosis.* Am J Pathol, 2006. 169(4): p. 1155-66.
27. Petrache, I., et al., *A novel antiapoptotic role for alpha1-antitrypsin in the prevention of pulmonary emphysema.* Am J Respir Crit Care Med, 2006. 173(11): p. 1222-8.
28. Song, S., et al., *Recombinant adeno-associated virus-mediated alpha-1 antitrypsin gene therapy prevents type I diabetes in NOD mice.* Gene Ther, 2004. 11(2): p. 181-6.
29. Lu, Y., et al., *Alpha1-antitrypsin gene therapy modulates cellular immunity and efficiently prevents type I diabetes in nonobese diabetic mice.* Hum Gene Ther, 2006. 17(6): p. 625-34.
30. Lewis, E. C., et al., *Alpha1-antitrypsin monotherapy prolongs islet allograft survival in mice.* Proc Natl Acad Sci USA, 2005. 102(34): p. 12153-8.
31. Koulmanda, M., et al., *Curative and beta cell regenerative effects of alpha1-antitrypsin treatment in autoimmune diabetic NOD mice.* Proc Natl Acad Sci USA, 2008. 105(42): p. 16242-7.
32. Lewis, E. C., et al., *alpha1-Antitrypsin monotherapy induces immune tolerance during islet allograft transplantation in mice.* Proc Natl Acad Sci USA, 2008. 105(42): p. 16236-41.
33. Crystal, R. G., *The alpha 1-antitrypsin gene and its deficiency states.* Trends Genet, 1989. 5(12): p. 411-7.
34. Chao, H., et al., *Sustained and complete phenotype correction of hemophilia B mice following intramuscular injection of AAV1 serotype vectors.* Mol Ther, 2001. 4(3): p. 217-22.
35. Flotte, T. R., et al., *Preclinical characterization of a recombinant adeno-associated virus type 1-pseudotyped vector demonstrates dose-dependent injection site inflammation and dissemination of vector genomes to distant sites.* Hum Gene Ther, 2007. 18(3): p. 245-56.

What we claim is:

1. An adeno-associated virus (AAV) vector for transferring a small peptide coding sequence to a first cell for expression of the small peptide within the first cell and delivery of the small peptide to surrounding cells in a tissue, wherein the tissue is a retinal tissue, the AAV vector comprising:
   (i) a secretory signal sequence encoding a secretory signal peptide, wherein the secretory signal sequence consists of SEQ ID NO: 4;
   (ii) a sequence encoding a carrier protein;
   (iii) a sequence encoding a cleavage site; and
   (iv) a sequence encoding a small peptide less than 50 amino acids in length, wherein said small peptide is Angiotensin (Ang)1-7,
   wherein the secretory signal sequence, the sequence encoding the carrier protein and the sequence encoding the cleavage site are operatively associated with the sequence encoding the small peptide, and
   further wherein the AAV vector provides continuous secretion of the small peptide to cells distant from the first cell.

2. The AAV vector of claim 1, wherein the secretory signal sequence is 5' to the sequence encoding the carrier protein, the sequence encoding the cleavage site, and the sequence encoding the small peptide.

3. The AAV vector of claim 1, wherein the sequence encoding the cleavage site encodes a furin cleavage site.

4. The AAV vector of claim 1, wherein said carrier protein is albumin.

5. The AAV vector of claim 1, wherein said carrier protein is alpha-1-antitrypsin.

6. The AAV vector of claim 1, wherein said carrier protein is a heat shock protein, an Advanced Glycation End-product, or a pro-renin receptor.

7. The AAV vector of claim 1, wherein elements (i)-(iv) are arranged in a 5'-3' order on a polynucleotide molecule.

8. The AAV vector of claim 1, wherein said cleavage site is a site cleaved by PC1/3, PC2, PO4, P05/6, PACE4, SKI-1/S1P, NARC-1/PCSK9, thrombin or factor Xa.

9. A pharmaceutical composition comprising the AAV vector of claim 1 in a pharmaceutically acceptable carrier.

10. The AAV vector of claim 1, wherein the AAV vector is contained within an AAV viral particle.

11. The AAV vector of claim 1, wherein the cells distant from the first cell are retinal vascular endothelial cells.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetic Polypeptide

<400> SEQUENCE: 1
accagatctc gcaagaagcg c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Polypeptide

```
<400> SEQUENCE: 2
gcgcttcttg cgagatctgg t                                              21

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 3

Thr Arg Ser Arg Lys Lys Arg
1               5

<210> SEQ ID NO 4
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 4

Met Glu Thr Asp Thr Leu Leu Leu Trp Val Leu Leu Leu Trp Val Pro
1               5                   10                  15

Gly Ser Thr Gly Asp
            20

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Asp Arg Val Tyr Ile His Pro
1               5

<210> SEQ ID NO 6
<211> LENGTH: 21
<212> TYPE: DNA
<213> ORGANISM: Artificial Sequence
<220> FEATURE:
<223> OTHER INFORMATION: Synthetic Polypeptide

<400> SEQUENCE: 6
gaccgcgtgt acatccaccc c                                              21

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Asp Arg Val Tyr Ile His Pro Phe
1               5
```